United States Patent
Duerfeldt et al.

(10) Patent No.: US 12,319,708 B2
(45) Date of Patent: *Jun. 3, 2025

(54) AGONISTS OF PEROXISOME PROLIFERATOR-ACTIVATED RECEPTOR ALPHA (PPARα) AND METHODS OF USE

(71) Applicant: The Board of Regents of the University of Oklahoma, Norman, OK (US)

(72) Inventors: Adam Duerfeldt, Norman, OK (US); Xiaozheng Dou, Norman, OK (US); Ziwei Hu, St. Paul, MN (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,715

(22) Filed: Oct. 13, 2023

(65) Prior Publication Data

US 2024/0425534 A1 Dec. 26, 2024

Related U.S. Application Data

(63) Continuation of application No. 17/876,243, filed on Jul. 28, 2022, which is a continuation-in-part of application No. 16/981,483, filed as application No. PCT/US2019/022400 on Mar. 15, 2019, now Pat. No. 11,447,452.

(60) Provisional application No. 62/643,998, filed on Mar. 16, 2018.

(51) Int. Cl.
*A61P 29/00* (2006.01)
*C07F 9/30* (2006.01)
*C07F 9/38* (2006.01)

(52) U.S. Cl.
CPC ............ *C07F 9/3808* (2013.01); *A61P 29/00* (2018.01); *C07F 9/301* (2013.01)

(58) Field of Classification Search
CPC ......... A61P 29/00; C07F 9/3808; C07F 9/301
See application file for complete search history.

(56) References Cited

U.S. PATENT DOCUMENTS

| | | |
|---|---|---|
| 9,199,980 B2 | 12/2015 | Armani et al. |
| 2006/0069013 A1 | 3/2006 | Ostergaard et al. |
| 2008/0200535 A1 | 8/2008 | Ohmori et al. |

FOREIGN PATENT DOCUMENTS

| | | |
|---|---|---|
| JP | 2006516966 A | 7/2006 |
| JP | 2007509921 A | 4/2007 |
| JP | 2007523842 A | 8/2007 |
| JP | 2009269819 A | 11/2009 |
| WO | 2001092201 A1 | 2/2001 |
| WO | 2002044127 A1 | 6/2002 |
| WO | 2003027081 A2 | 4/2003 |
| WO | 2004056347 A2 | 7/2004 |
| WO | 2004080480 A1 | 9/2004 |
| WO | 2005026134 A1 | 3/2005 |
| WO | 2005040104 A1 | 5/2005 |
| WO | 2006069013 A1 | 6/2006 |
| WO | 2008121570 A1 | 10/2008 |
| WO | 2017044551 A1 | 3/2017 |

OTHER PUBLICATIONS

Krecmerova, Frontiers In Chemistry, May 2022, vol. 10, article 889737, 1-28. (Year: 2022).*
Database Registry (online); xp002805440; Chemical Abstracts Service; Database accession No. 1794804-78-6; 1 page (abstract only).
Database Registry (online); xp002805441; Chemical Abstracts Service; Database accession No. 1243492-34-3; 1 page (abstract only).
Database Registry (online); xp002805442; Chemical Abstracts Service; Database accession No. 886621-11-0; 1 page (abstract only).
Database Registry (online); xp002805443; Chemical Abstracts Service; Database accession No. 884996-01-4; 1 page (abstract only).
Database Registry (online); xp002805454; Chemical Abstracts Service; Database accession No. 475597-54-7; 1 page (abstract only).
Link, J.T., et al.; "Optimization and metabolic stabilization of a class of nonsteroidal glucocorticoid modulators"; Bioorganic & Medicinal Chemistry Letters 14 (2004) 4169-4172.
Brauer, S., et al.; "Evolutionary Chemistry Approach toward Finding Novel Inhibitors of the Type 2 Diabetes Target Glucose-6-phosphate Translocase"; J. Comb. Chem. 7 (2005) 218-226.
Link, J.T., et al.; "Antidiabetic Activity of Passive Nonsteroidal Glucocorticoid Receptor Modulators"; J. Med. Chem. 46:16 (2005) 5295-5304.
Yang, M., et al.; "Neutrophil- and Myeloperoxidase-Mediated Metabolism of Reduced Nimesulide: Evidence for Bioactivation"; Chem. Res. Toxicol. 23 (2010) 1691-1700.
Database Registry (online); xp002805440; Chemical Abstracts Service; Database accession No. 1794804-78-6; Jul. 5, 2015; 1 page (abstract only).
Zhang, S., et al.; "Role of Peroxisome Proliferator-Activated Receptor y in Ocular Diseases"; Journal of Ophthalmology (2015) Article ID 275435; 10 pages.
Korczynska, M., et al.; "Docking and Linking of Fragments To Discovery Jumonji Histone Demethylase Inhibitors"; J. Med. Chem. 59:4 (2016) 1580-1598.

(Continued)

*Primary Examiner* — D Margaret M Seaman
(74) *Attorney, Agent, or Firm* — Hall Estill Law Firm

(57) ABSTRACT

Benzyl derivative compounds having peroxisome proliferator-activated receptor α (PPARα) agonistic activity, kits and compositions containing such compounds, and methods of their use in enhancing PPARα activity for treating diseases and/or conditions involving inflammation and/or angiogenesis, particularly ocular diseases and/or conditions such as but not limited to retinal inflammation, retinal neovascularization, retinal vascular leakage, retinopathy of prematurity, diabetic retinopathy, age-related macular degeneration, and diabetic macular edema.

22 Claims, 8 Drawing Sheets

(56) References Cited

OTHER PUBLICATIONS

Dou, X-Z., et al.; "Structure-guided evolution of a 2-phenyl-4-caroxyquinoline chemotype into PPARa selective agonists: New leads for oculovascular conditions"; Bioorganic & Medicinal Chemistry Letters 28 (2018) 2717-2722.
CN2019800289050; "First office action notification"; 2019; 9 pages (translation).
PCT/US2019/022400; International Search Report and Written Opinion; Jul. 16, 2019; 15 pages.
Dou, et al.; "Evolution of a 4-Benzyloxy-benzylamino Chemotype to Provide Efficacious, Potent, and Isoform Selective PPARa Agonists as Leads for Retinal Disorders"; J. Med. Chem. 63 (2020) 2854-2876.
JP2020549044; Office Action; 2020; 8 pages.
U.S. Appl. No. 16/981,483; Non-Final Office Action; Sep. 10, 2021; 18 pages.
U.S. Appl. No. 16/981,483; Response to Non-Final Office Action; Feb. 16, 2022; 17 pages.
EP19766610; Supplementary European Search Report; European Patent Office; Jan. 26, 2022; 4 pages.
Chinese First Office Action; CN201980028905.0; dated Mar. 9, 2023; 6 pages (English translation).
Database Registry; RN1827326-82-8, RN1243837-89-9, RN886621-11-0, RN1243834-33-4, RN1243831-48-2, RN1243830-48-9, RN1243829-86-8, RN1243826-62-1, RN1243824-48-7, RN1243821-81-9, RN1243813-37-7, 1243804-43-4, RN1243796-88-4, RN1243782-52-6, RN1243779-71-6, RN124379-41-8, RN1243736-19-7, RN1243734-12-4, RN1243730-92-8, RN1243708-65-7, RN1243689-67-9, RN1243681-48-2, RN1243666-61-6, RN1243666-09-2, RN1243661-34-8, RN1243639-06-6, RN1243620-53-2, RN1243618-97-4, RN1243583-00-7, RN1243578-91-7, RN1243568-38-8, RN1243535-99-0, RN1243533-02-9, RN1243528-98-4, RN1243518-27-5, RN1243517-02-3, RN1243508-99-7, RN1243496-48-1, RN885004-83-1, RN885003-80-5, RN885000-18-0, RN885000-09-9, RN885000-00-0, RN884999-96-6, RN884999-88-6, RN884999-80-8, RN884999-73-9, RN884999-68-2, RN884999-59-1, RN884999-51-3, RN884999-42-2, RN884999-37-5, RN884999-28-4, RN884999-18-2, RN884999-09-1, RN884999-05-7, RN884996-61-6, RN884989-28-0; Chemical Library; Copyright 2023; 32 pages.
Translation of Second Office Action; Chinese Application No. 201980028905.0; date of issuance: Oct. 25, 2023; 6 pages.

\* cited by examiner

AGONISTS OF PEROXISOME PROLIFERATOR-ACTIVATED RECEPTOR ALPHA (PPARα) AND METHODS OF USE

CROSS-REFERENCE TO RELATED APPLICATIONS

The present patent application is a continuation of U.S. application Ser. No. 17/876,243, filed Jul. 28, 2022, which is a continuation-in-part of U.S. application Ser. No. 16/981,483, filed Sep. 16, 2020, which is a national stage version of PCT/US2019/022400, filed Mar. 15, 2019, which claims the benefit of U.S. Ser. No. 62/643,998, filed on Mar. 16, 2018, under 35 U.S.C. 119(e). The entire contents of each of the above applications is hereby expressly incorporated herein by reference.

GOVERNMENT SUPPORT

This invention was made with government support under Grant Number R21EY028279 awarded by the National Eye Institute of the National Institutes of Health (NIH). The government has certain rights in the invention.

BACKGROUND

Retinal inflammation and resultant neovascularization (NV) are major causes of vision loss in a number of ocular disorders such as retinopathy of prematurity (ROP), diabetic retinopathy (DR) and age-related macular degeneration (AMD). Diabetic macular edema (DME) is caused by retinal vascular leakage and is the primary cause of vision loss in diabetic eye disease. Accumulating evidence suggests that DR is a chronic inflammatory disorder, as multiple inflammatory factors such as tumor necrosis factor-alpha (TNF-α), intercellular adhesion molecule-1 (ICAM-1), and vascular endothelial growth factor (VEGF) are over-expressed in the diabetic retina. Inflammation plays a causative role in impaired retinal vascular endothelial function, vascular leakage and later retinal NV. Anti-VEGF has emerged as a primary treatment option, but suffers from the requirement of frequent intraocular injections, high cost, and the need for specialized facilities. Additionally, although effective for most, ~40-50% of patients are refractory to intravitreal injection of anti-VEGF and corticosteroids. This implies that auxiliary pathways and factors that remain unaddressed with current interventions are involved in disease causation and progression.

The peroxisome proliferator-activated receptors (PPARs) are a family of nuclear hormone-activated receptors and transcription factors. The PPAR family includes three members, PPAR alpha (PPARα), PPAR gamma (PPARγ), and PPAR delta (PPARδ), the latter of which is sometimes referred to in the art as PPAR beta (PPARβ). Although these three PPAR members share significant sequence homology, they have different tissue distributions, diverse functions, and can be selectively targeted. While PPARγ is primarily expressed in adipose tissue, PPARα is expressed in cells with high mitochondrial activities including the liver, vascular endothelial cells (ECs), smooth muscle cells, kidney and heart. Preliminary studies have shown that PPARα is abundantly expressed in the retina. Only recently, however, have the roles of PPARα in regulating inflammation, apoptosis, and neovascularization (NV) in diabetic retinas been revealed, establishing a new avenue for PPARα agonists as therapeutics for oculovascular diseases. Upon activation by endogenous or exogenous synthetic agonists, PPARα forms a heterodimer with retinoid x receptor (RXR) and binds to the PPAR responsive element (PPRE) in the promoter of its target genes activating target gene transcription. In addition, PPARα indirectly regulates other genes by interfering with their transcriptional regulation. PPARα has been shown to regulate a large number of genes involved in lipid metabolism and vascular inflammation such as nuclear factor kappa-light-chain-enhancer of activated B cells (NF-κB), ICAM-1 and interleukin-6 (IL-6). Furthermore, PPARα has been shown to regulate oxidation and angiogenesis. However, the function of PPARα in the retina is poorly understood. The role of PPARα in DR was unrecognized until findings from the FIELD and ACCORD clinical trials demonstrated that the PPARα agonist fenofibric acid (a metabolite of fenofibrate) had a robust and unanticipated therapeutic effect on DR, reducing the need for laser treatment by 32-40% in type 2 diabetic patients. Previous studies have demonstrated that PPARα levels are decreased in the retinas of both type 1 and type 2 diabetic animal models. Furthermore, activation of PPARα by fenofibrate effectively reduced retinal leukostasis and vascular leakage in diabetic models and ameliorates ischemia-induced retinal NV.

Fenofibrate was originally recognized for its ability to lower cholesterol and triglyceride levels and has thus been widely used clinically for the treatment of hyperlipidemia for more than 30 years. Fenofibrate is the first low-cost and safe oral drug for DR with clinically proven efficacy against NV and DME in DR patients and is thus of great interest to clinicians, basic scientists and pharmaceutical companies interested in the development of novel DR therapeutics. It has been reported that the protective effects of fenofibrate on retinal NV and DME are not correlated with its lipid-lowering activity, but rather arise from interaction of its metabolite, fenofibric acid, with PPARα. Fenofibrate thus has significant therapeutic potential in the treatment of DR and AMD, but has a relatively low binding affinity for PPARα, and has off-target nephrotoxic effects and other potential side effects. A critical need exists to develop new treatment options that are non-invasive and complementary to current approaches. Development of higher affinity agonists of PPARα to further improve the treatment for DR and other inflammatory and angiogenic disorders of the eye and elsewhere in the body is desirable and is the goal to which the present work is directed.

DETAILED DESCRIPTION

Figure 1:
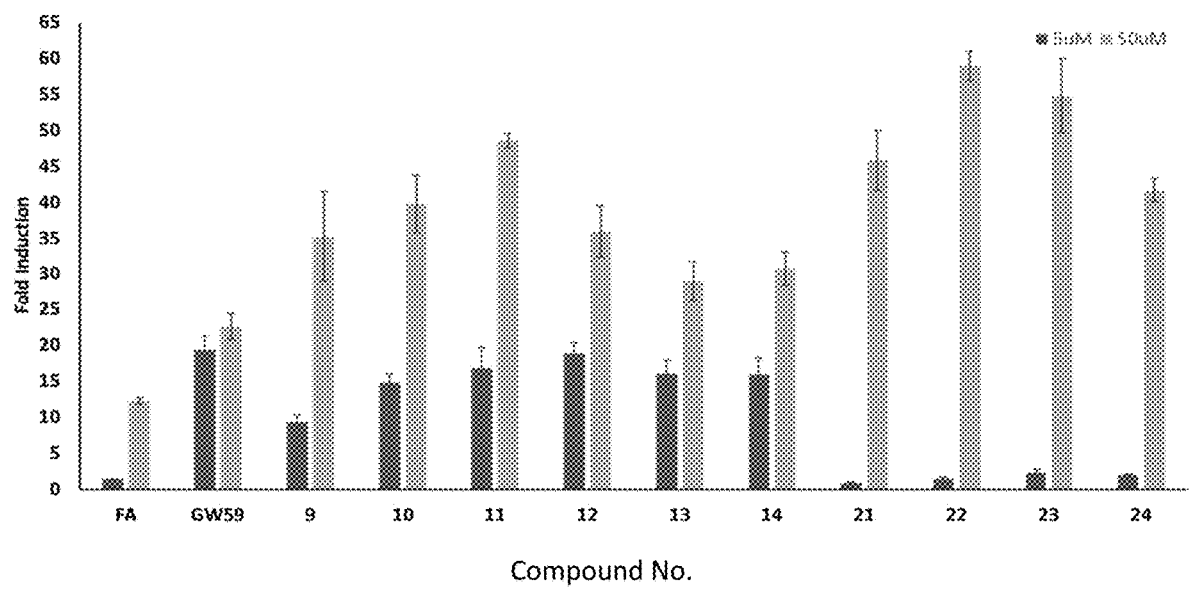
FIG. 1 shows initial evaluation results of compounds 9-14 and 21-24 for hPPARα agonism in a cell-based luciferase assay. Results are presented from a single experiment as fold-induction versus the DMSO control±S.E. (n=3). Compound GW590735 was evaluated at 5 µM and 10 µM.

As noted above, retinal inflammation and neovascularization are major causes of vision loss in a number of ocular disorders such as retinopathy of prematurity, diabetic retinopathy (DR), and age-related macular degeneration (AMD). Two large, prospective clinical studies reported that fenofibrate, an agonist of PPARα, has robust therapeutic effects in DR. Disclosed herein is a new class of compounds which, due to PPARα agonistic activity, have an effect on retinal endothelial dysfunction, angiogenesis and inflammation, indicating a therapeutic effect in, for example, DR and AMD (e.g., wet AMD). The compositions of the present disclosure may be used in treatments for ocular disorder or conditions such as, but not limited to, DR, AMD (e.g., wet AMD), retinal inflammation, retinal neovascularization (NV), retinal vascular leakage, retinopathy of prematurity (ROP), and diabetic macular edema (DME). Other diseases and/or conditions associated with inflammation and/or angiogenesis which can be treated using the compounds of the present disclosure are described below.

Before further describing various embodiments of the compounds, compositions and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods of production and application and use thereof disclosed herein can be made and executed in light of the present disclosure. Thus, while the compounds, compositions, and methods of the present disclosure have been described in terms of particular embodiments, it will be apparent to those of skill in the art that variations may be applied to the compounds, compositions and/or methods and in the steps or in the sequence of steps of the methods described herein without departing from the concept, spirit, and scope of the inventive concepts described herein.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one." but it is also consistent with the meaning of "one or more." "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, as well as 1.1, 1.2, 1.3, 1.4, 1.5, etc., 2.1, 2.2, 2.3, 2.4, 2.5, etc., and so forth, where the range is not limited solely to integers. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. Appearances of the phrase "in one embodiment" in various places in the specification are not necessarily all referring to the same embodiment and are not necessarily limited to a single or particular embodiment.

Where used herein, the pronoun "we" is intended to refer to all persons involved in a particular aspect of the investigation disclosed herein and as such may include non-inventor laboratory assistants and collaborators working under the supervision of the inventor.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

The term "active agent" as used herein is intended to refer to a substance which possesses a biological activity relevant to the present disclosure, and particularly refers to therapeutic and diagnostic substances which may be used in methods described in the present disclosure. An active agent may be a compound that is useful for the purposes disclosed herein.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Examples of animals or mammals within the scope and meaning of the term subject or patient include but are not limited to dogs, cats, rats, mice, rabbits, guinea pigs, chinchillas, horses, goats, pigs, cattle, sheep, llamas, alpacas, zoo animals, Old and New World monkeys, non-human primates, and humans.

In at least certain embodiments, the disease and/or condition which can be treated with a compound of the present disclosure is characterized by inflammation and/or angiogenesis. Such diseases and/or conditions having an inflammatory basis which can be treated with a compound of the present disclosure, include, but are not limited to, inflammatory bowel disease, type 1 diabetes, type 2 diabetes, Graves disease, multiple sclerosis, various types of arthritis, vasculitis, dermatitis, glomerulonephritis, hepatitis, periodonititis, atherosclerosis, heart failure, obesity, Alzheimer's disease, and metabolic syndrome, and other disorders and conditions disclosed herein.

Examples of ocular diseases having an inflammatory basis which can be treated with a compound of the present disclosure, include, but are not limited to, keratitis, endophthalmitis, blepharitis, conjunctivitis, scleritis, herpetic inflammation, uveitis, vasculitis, arteritis, orbital inflammations, optic neuritis, sympathetic ophthalmia, retinitis, and other autoimmune diseases, age-related macular degeneration, macular edema, diabetic retinopathy, glaucoma, proliferative vitreoretinopathy, corneal edema, uveal edema, and retinal edema.

Diseases and/or conditions having an angiogenic basis which can be treated with a compound of the present disclosure, include, ocular diseases and/or conditions such as, but not limited to, diabetic retinopathy, age-related macular degeneration, retinopathy of prematurity, retinal artery or vein occlusion, corneal graft rejection, corneal neovascularization, neovascular glaucoma and sickle cell retinopathy, and non-ocular diseases and/or conditions including, but not limited to, cancer, skin diseases, diabetic ulcers, diabetic nephropathy, cardiovascular disease and stroke.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be formulated with carrier compounds which provide delayed, controlled, extended, and/or sustained release, for example using formulation techniques which incorporate the active agent into a degradable polymer.

The term "topical" is used herein to define a mode of administration through an epithelial surface, such as but not limited to, a material that is administered by being applied externally to the eye. A non-limiting example of topical administration is through the use of eyedrops, or application of active agent-containing particles.

The terms "therapeutic composition" and "pharmaceutical composition" refer to composition comprising a compound of the present disclosure (also referred to herein as an active agent) that may be administered to a subject by any method known in the art or otherwise contemplated herein, wherein administration of the composition brings about a therapeutic effect as described elsewhere herein. As noted, the compositions of the present disclosure may be designed to provide delayed, controlled, extended, and/or sustained release using appropriate formulation techniques.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein. The term "activity-enhancing amount" refers to an amount of an active agent which is sufficient to increase PPARα activity in a cell or subject.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

As used herein, the term "phosphate" refers to the moiety:

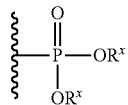

wherein each $R^x$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine. In certain embodiments one $R^x$=H or a salt thereof, and one $R^x{\neq}H$. In certain embodiments, both $R^x$=H or salts thereof.

As used herein the term "phosphonate" refers to the moiety:

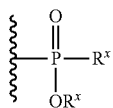

wherein each $R^x$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine. In certain embodiments, the $R^x$ of the —$OR^x$=H or salts thereof. In certain embodiments, the $R^x$ of the —$OR^x{\neq}H$.

Where used herein the term "compound" refers to a chemical substance comprising two or more different elements. The term compound also includes isomers and tautomers of the compound, solvates of the compound, and solvates of the isomers and tautomers of the compound.

The term isomer" includes conformational isomers, geometric isomers, stereoisomers and/or optical isomers. For example, the compounds of the present disclosure may include one or more chiral centers and/or double bonds and as a consequence may exist as stereoisomers, such as double-bond isomers (i.e., geometric isomers), enantiomers, diastereomers, and mixtures thereof, such as racemic mixtures. "Stereoisomers" are compounds that differ in the chirality of one or more stereocenters. Stereoisomers include enantiomers and diastereomers.

"Tautomer" refers to alternate forms of a compound that differ in the position of a proton, such as the enol form, the keto form, and mixtures thereof. The tautomers may be imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term "linker" as used herein refers to a divalent saturated or unsaturated aliphatic or aromatic hydrocarbyl group which may include heteroatoms and are unsubstituted or substituted with from 1 to 5, preferably 1 to 3, or more preferably 1 to 2 substituents selected from the group consisting of alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio.

Where used herein the terms alkyl, haloalkyl, alkoxyl, haloalkoxyl, alkenyl, and alkynyl are generally intended to refer to branched or unbranched structures comprising 1, 2, 3, 4, 5, 6, 7, 8, 9, or 10 carbons, unless otherwise designated. Haloalkyl may refer to, for example, a 1, 2, 3, 4, 5, 6, 7, 8, 9, or 10 carbon haloalkyl having 1 to 3 halogen atoms. Haloalkoxyl may refer to, for example, a 1, 2, 3, 4, 5, 6, 7, 8, 9, or 10 carbon haloalkyl having 1 to 3 halogen atoms. A halogen may refer to chlorine (Cl), fluorine (F), bromine (Br), and/or iodine (I). Halogen may be abbreviated as "halo" herein.

"Alkyl" refers to monovalent saturated aliphatic hydrocarbyl groups having from 1 to 10 carbon atoms and more particularly 1 to 6 carbon atoms. This term includes, by way of example but not limitation, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to monovalent straight or branched hydrocarbyl groups having from 2 to 6 carbon atoms and more particularly 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and more particularly 2 to 3 carbon atoms and having at least 1 and more particularly from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more particularly 1 to 2 substituents selected from the group consisting of alkoxy, substituted alkoxy, acyl, acylamiiio, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and more particularly 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and more particularly 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryl oxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups having from 1 to 6 and more particularly 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$— or —$CH(CH_3)CH_2$—), butylene (—$CH_2CH_2CH_2CH_2$—), isobutylene (—$CH_2CH(CH_3)CH_2$—), sec-butylene (—$CH_2CH_2(CH_3)CH$—), and the like.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or has from 1-3 carbon atoms replaced with —O—, —S—, or —NR— moieties where R is H or $C_1$-$C_6$ alkyl. When the alkylene is substituted by an oxo group, 2 hydrogens attached to the same carbon of the alkylene group are replaced by "═O".

"Alkoxy" refers to the group-O-alkyl wherein alkyl is as defined herein. Alkoxy includes, by way of example, but not limitation, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H-C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl also includes the "acetyl" group $CH_3C(O)$—.

"Acylamino" refers to the groups —$NR^aC(O)$alkyl, —$NR^aC(O)$substituted alkyl, —$NR^aC(O)$cycloalkyl, —$NR^aC(O)$substituted cycloalkyl, —$NR^aC(O)$cycloalkenyl, —$NR^aC(O)$substituted cycloalkenyl, —NRC(O)alkenyl, —NRC(O)substituted alkenyl, —$NR^aC(O)$alkynyl, —$NR^aC(O)$substituted alkynyl, —$NR^aC(O)$aryl, —$NR^aC(O)$substituted aryl, —$NR^aC(O)$heteroaryl, —$NR^aC(O)$substituted heteroaryl, —NRC(O)heterocyclic, and —$NR^aC(O)$ substituted heterocyclic wherein $R^a$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O-wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH2-.

"Substituted amino" refers to the group —$NR^bR^c$ where $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SC-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic, and wherein $R^b$ and $R^c$ are optionally joined, together with the nitrogen bound thereto to form a heterocyclic or substituted heterocyclic group, provided that $R^b$ and $R^c$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^b$ is hydrogen and $R^c$ is alkyl, the substituted amino group is sometimes referred to herein as alkylamino. When $R^b$ and $R^c$ are alkyl, the substituted amino group is sometimes referred to herein as dialkylamino. When referring to a monosubstituted amino, it is meant that only one of $R^b$ or $R^c$ is hydrogen. When referring to a disubstituted amino, it is meant that neither $R^b$ nor $R^c$ are hydrogen.

"Aminocarbonyl" refers to the group —C(O)NR$^b$R$^c$ where $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^b$R$^c$ where $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^a$C(O)NR$^b$R$^c$ where $R^a$ is hydrogen or alkyl and $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^a$C(S)NR$^b$R$^c$ where $R^a$ is hydrogen or alkyl and $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^b$R$^c$ where $R^b$ and $R^c$ arc independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^b$R$^c$ where $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, herocyclic, and substituted heterocyclic are as defined herein.

"Aminosulfonyloxy" refers to the group —O—SO$_2$NR$^b$R$^c$ where $R^b$ and R are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^a$SO$_2$NR$^b$R$^c$ where $R^a$ is hydrogen or alkyl and $R^b$ and $R^c$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^d$)NR$^b$R$^c$ where $R^b$, $R^c$, and $R^d$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^b$ and $R^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring {e.g., phenyl} or multiple condensed rings {e.g., naphthyl or anthryl} which condensed rings may or may not be aromatic {e.g., 2-benzoxazolinone, 2H-1,4-benzoxazin-3(4H)-one-7-yl, and the like} provided that the point of attachment is at an aromatic carbon atom. Aryl groups include for example phenyl and naphthyl.

"Substituted aryl" refers to aryl groups which are substituted with 1 to 5, such as 1 to 3, and more particularly 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester) amino" refers to the group —$NR^aC(O)$O-alkyl, —$NR^aC(O)$O-substituted alkyl, —$NR^aC(O)$O-alkenyl, —$NR^aC(O)$O-substituted alkenyl, —$NR^aC(O)$O-alkynyl, —NRC(O)O-substituted alkynyl, —$NR^aC(O)$O-aryl, —$NR^aC(O)$O-substituted aryl, —$NR^aC(O)$O-cycloalkyl, —$NR^aC(O)$O-substituted cycloalkyl, —$NR^aC(O)$O-cycloalkenyl, —$NR^aC(O)$O-substituted cycloalkenyl, —$NR^aC(O)$O-heteroaryl, —$NR^aC(O)$O-substituted heteroaryl, —$NR^aC(O)$O-heterocyclic, and —$NR^aC(O)$O-substituted heterocyclic wherein $R^a$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O-C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non-aryl part is joined to the rest of the molecule. Examples of suitable cycloalkyl groups include, but are not limited to, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation, such as from 1 to 2 sites of >C=C< ring unsaturation.

"Substituted cycloalkyl" and "substituted cycloalkenyl" refers to a cycloalkyl or cycloalkenyl group having from 1 to 5, 1 to 4, or 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Cycloalkyloxy" refers to —O-cycloalkyl. "Substituted cycloalkyloxy refers to —O— (substituted cycloalkyl). "Cycloalkylthio" refers to —S-cycloalkyl. "Substituted cycloalkylthio" refers to —S-(substituted cycloalkyl). "Cycloalkenyloxy" refers to —O-cycloalkenyl. "Substituted cycloalkenyloxy" refers to —O-(substituted cycloalkenyl). "Cycloalkenylthio" refers to —S-cycloalkenyl. "Substituted cycloalkenylthio" refers to —S-(substituted cycloalkenyl).

"Guanidino" refers to the group —NHC(=NH)NH$_2$. "Substituted guanidino" refers to —NR$^a$C(=NR$^e$)N(R$^e$)$_2$ where each R$^e$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^e$ groups attached to a common guanidino nitrogen atom are optionally joined together with the nitrogen bound thereto to form a heterocyclic or substituted heterocyclic group, provided that at least one R$^e$ is not hydrogen, and wherein said substituents are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Non-limiting examples of heteroaryls include pyridinyl, pyrrolyl, indolyl, thiophenyl, and furanyl.

"Substituted heteroaryl" refers to heteroaryl groups that are substituted with from 1 to 5, 1 to 4, 1 to 3, or 1 to 2 substituents selected from the group consisting of the same group of substituents defined for substituted aryl.

"Heteroaryloxy" refers to —O-heteroaryl. "Substituted heteroaryloxy" refers to the group —O-(substituted heteroaryl).

"Heteroarylthio" refers to the group —S-heteroaryl. "Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of N, S, and O. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5, 1 to 4,or 1 to 3 of the same substituents as defined for substituted cycloalkyl.

"Heterocyclyloxy" refers to the group —O-heterocycyl. "Substituted heterocyclyloxy" refers to the group —O-(substituted heterocycyl).

"Heterocyclylthio" refers to the group —S-heterocycyl. "Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the double-bonded atom (=O).

"Phenylene" refers to a divalent aryl ring, where the ring contains 6 carbon atoms. Substituted phenylene refers to phenylenes which are substituted with 1 to 4, 1 to 3, or 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy. aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

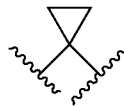

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein. "Substituted alkylthio" refers to the group —S-(substituted alkyl) wherein substituted alkyl is as defined herein.

Where used herein, the term "salt" refers to a chemical compound comprising an ionic assembly of a negatively-charged moiety (the phosphate/phosphonate compound) and a positively charged cationic atom or compound, which results in a compound with no net electric charge. The salts of the present disclosure are intended to be pharmaceutically-acceptable, i.e., salts which are suitable for pharmaceutical use. Generally, pharmaceutically-acceptable salts are those salts that retain substantially one or more of the desired pharmacological activities of the parent compound and which are suitable for administration to humans or other animals as defined elsewhere herein. The cations of the phosphate and phosphonate salt compounds of the present disclosure include but are not limited to a metal ion, such as a alkali metal ion (e.g., sodium, potassium, lithium), an alkaline earth metal ion (e.g., magnesium, calcium, barium), or an aluminum ion. The cation may be an ammonium ion, a quaternary alkylammonium, a quaternary arylammonium, or an ammonium ion derived from an organic base, including but not limited to ethanolamine, diethanolamine, triethanolamine, N-methylglucamine, morpholine, piperidine, pyridine, dimethylamine, diethylamine, trimethylamine, triethylamine, isopropylamine, 2-ethylamino ethanol, histidine, lysine, procaine, and Tris (2-amino-2-(hydroxymethyl) propane-1,3-diol).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

Where used herein, the term "prodrug" refers to art-recognized modifications to one or more functional groups, such that the functional groups are metabolized in vivo to provide an active agent or an active metabolite thereof. Such functional groups are well known in the art including acyl or thioacyl groups for hydroxyl and/or amino substitution, conversion of one or more hydroxyl groups to the monophosphate, diphosphate and triphosphate wherein optionally one or more of the pendent hydroxyl groups of the monophosphate, diphosphate and triphosphate have been converted to an alkoxy, a substituted alkoxy, an aryloxy, or a substituted aryloxy group, and the like.

The prodrug derivative may demonstrate various pharmacologically desirable properties, such as but not limited to increased aqueous solubility, increased bioavailability, and altered activity of the active agent. By "biologically active" is meant the ability to modify the physiological system of a cell, tissue, or organism without reference to how the active agent has its physiological effects. Such prodrugs may, but need not, be pharmacologically inactive until converted into their active drug form. The compounds disclosed herein can include prodrug derivatives that are hydrolyzed or otherwise cleaved under the conditions of use.

Examples of suitable prodrug derivatives of the present disclosure include, but are not limited to, active agents where a hydroxyl, amino, thiol or a carboxyl group is derivatized to form the prodrug. For example, a hydroxyl functional group, including phenolic and aliphatic hydroxyl groups, can be masked as a phosphate, phosphonate, sulfonate, ester, or with a carbonate-containing progroup. As used herein, the progroup refers to a group that is bonded to an active agent to provide a prodrug derivative. These prodrugs can be hydrolyzed in vivo to provide the hydroxyl group. An amino functional group can be masked as an amide, carbamate, imine, urea, phosphenyl, phosphoryl, or sulfenyl progroup. These prodrugs can be hydrolyzed in vivo to provide the amino group. A carboxyl group can be masked as an ester (including silyl esters and thioesters), amide, or oxadiazole progrtoup. These prodrugs can be hydrolyzed in vivo to provide the carboxyl group.

The prodrugs can increase the water solubility of the prodrug compared to the active agent. Thus, the progroup(s), such as for example a phosphate or a phosphonate moiety, or a linker containing a phosphate or a phosphonate moiety, may include or can be one or more groups suitable for imparting drug molecules with improved water solubility. Such groups are well-known and include, by way of example and not limitation, hydrophilic groups such as a phosphate or a phosphonate or an alkyl, aryl, and arylalkyl, or cycloheteroalkyl group substituted with one or more of a phosphorous acid (i.e., a phosphate or a phosphonate), an amine, alcohol, a carboxylic acid, a sulfoxide, a sugar, an amino acid, a thiol, a polyol, an ether, a thioether, and a quaternary amine salt. Examples of methods for synthesizing prodrugs, are described, e.g., in Ettmayer et al., (2004), J. Med. Chem. 47(10):2393-2404, and Bundgaard et al. (1989) J. Med. Chem. 32(12):2503-2507, and can be adapted for synthesizing the prodrug derivatives of the present disclosure by a skilled artisan upon reading this disclosure.

For example, various ester groups, including phosphates or phosphonates, commonly undergo acid-catalyzed hydrolysis to yield the parent hydroxyl group when exposed to the acidic conditions of the stomach or base-catalyzed hydrolysis when exposed to the basic conditions of the intestine or blood. Thus, when administered to a subject orally, compounds that include ester moieties can be considered prodrugs of their corresponding hydroxyl, regardless of whether the ester form is pharmacologically active. For example, prodrugs can cleave chemically in the stomach to form the active compounds, and can employ progroups including such esters. Alternatively, the progroups can be designed to metabolize in the presence of enzymes such as but not limited to phosphatases, esterases, amidases, lipolases, including ATPases and kinases. Progroups including linkages capable of metabolizing in vivo are well known and include, by way of example but not limitation, ethers, thioethers, silylethers, silylthioethers, esters, thioesters, carbonates, thiocarbonates, carbamates, thiocarbamates, ureas, thioureas, and carboxamides.

A prodrug may also be metabolized under the desired conditions of use, for example, under the acidic conditions found in the stomach and/or by enzymes found in vivo, to yield a biologically active group, such as the compounds as described herein. A skilled artisan will appreciate that the progroup can comprise virtually any known or later-discovered hydroxyl, amine or thiol protecting group. Examples of suitable protecting groups that can be used in the compounds of the present disclosure include, but are not limited to, those found in "Greene's Protective Groups in Organic Synthesis," P. G. M. Wuts, 5th Ed., Wiley, New York, 2014.

The identity of the progroup(s) can also be selected to impart the prodrug with desirable characteristics. For example, hydrophilic groups can be used to increase water solubility. In this way, prodrugs specifically tailored for selected modes of administration can be obtained. The prodrug may also assist, for example, in improved passive intestinal absorption, improved transport-mediated intestinal absorption, protection against fast metabolism (slow-release prodrugs), tissue-selective delivery, passive enrichment in target tissues, and targeting-specific transporters. Various groups described in these references can be utilized in the prodrugs described herein.

The present work demonstrates how the new class of compounds of the present disclosure can be used as, for example, ophthalmic compositions for the treatment of ocular disorders and conditions such as but not limited to retinal inflammation, retinal neovascularization, retinal vascular leakage, retinopathy of prematurity (ROP), diabetic retinopathy (DR), age-related macular degeneration (e.g., wet AMD), and diabetic macular edema (DME), and other ocular and non-ocular diseases and/or conditions described herein.

In certain non-limiting embodiments, the present disclosure includes a compound having the chemical structure I:

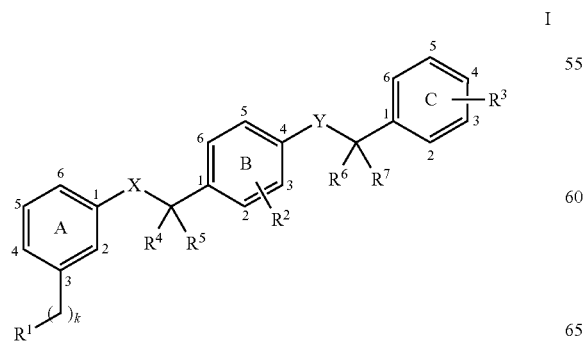

wherein ring A is a benzene, or a pyridine comprising nitrogen (N) in position 2, 4, 5, or 6;

wherein ring B is a benzene, or a pyridine comprising N in position 2, 3, 5, or 6;

wherein ring C is a benzene, or a pyridine comprising N in position 2, 3, 4, 5, or 6;

wherein X is selected from the group consisting of oxygen (O), NH, sulfur (S), and $CH_2$;

wherein Y is selected from the group consisting of O, NH, S, and $CH_2$;

wherein k is 0, 1, 2, 3, 4, 5, 6, 7, 8, 9, or 10 carbon atoms; and wherein in at least certain embodiments the $R^1$ substituent on the "A" ring of chemical structure I is selected from the chemical structures i-x shown in Table 1 below:

TABLE 1

Examples of $R^1$ substituents

| $R^1$ substituent no. | Chemical structure |
|---|---|
| i | ![structure](carboxylic acid) |
| ii | ![structure](hydroxamic acid) |
| iii | ![structure](N-acyl hydroxylamine) |
| iv | ![structure](phosphonic acid) |
| v | ![structure](H-phosphinic acid) |
| vi | 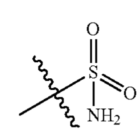 [SMILES: *S(N)(=O)=O] |
| vii | 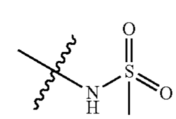 [SMILES: *NS(C)(=O)=O] |
| viii | 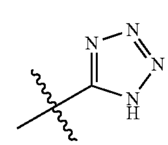 [SMILES: *c1nnn[nH]1] |

TABLE 1-continued

Examples of R¹ substituents

| R¹ substituent no. | Chemical structure |
|---|---|
| ix | X-C(R⁸)(R⁹)-C(=O)OH |
| x | B(OR¹⁰)(OR¹¹) |

In non-limiting embodiments, $R^8$ and $R^9$ of structure ix of Table 1 can be selected from the group: hydrogen (H), halogens (F, Cl, Br, I), alkyl (e.g., branched or unbranched, $C_1$ to $C_{10}$), alkoxy (e.g., branched or unbranched, $C_1$ to $C_{10}$), and cyclo ($R^8$ linked to $R^9$). In structure ix of Table 1, X can be O, NH, S, or $CH_2$. In non-limiting embodiments, $R^{10}$ and $R^{11}$ of structure x of Table 1 can be selected from the group: H, alkyl (e.g., branched or unbranched, $C_1$ to $C_{10}$), and cyclo ($R^{10}$ linked to $R^{11}$).

In other non-limiting examples, $R^1$ of chemical structure I can be selected from the group: carboxylic acids, and carboxylic acid isosteres including hydroxamic acids, hydroxamic esters, phosphonic acids, phosphinic acids, sulfonic acids, sulfinic acids, sulfonamides, acyl sulfonamides, sulfonylureas, acylureas, tetrazoles, thiazolidine diones, oxazolidine diones, oxadiazol-5(4H)-ones, thiadiazol-5(4H)-ones, oxathiadiazole-2-oxides, oxadiazol-5(4H)-thiones, isoxazoles, tetramic acids, cyclopentane 1,3-diones, cyclopentane 1,2-diones, squaric acids, substituted phenols, heteroarenes, amidines, hydroxyamides, alkyl hydroxyamidines, including the exemplary structures shown in Table 2, and further including salts of any of the above.

TABLE 2

Other examples of R¹

| Generic Group | Non-limiting examples, n = 0-4 |
|---|---|
| Carboxylic acids | –(CH₂)ₙ–C(=O)OH |
| Hydroxamic acids | –(CH₂)ₙ–C(=O)NH–OH |
| | –(CH₂)ₙ–N(OH)–C(=O)CH₃ |
| Hydroxamic esters | –(CH₂)ₙ–C(=O)NH–OMe |
| | –(CH₂)ₙ–O–NH–C(=O)CH₃ |
| Phosphonic acids | –(CH₂)ₙ–P(=O)(OH)₂ |
| Phosphinic acids | –(CH₂)ₙ–P(=O)(OH)(H) |
| Sulfonic acids | –(CH₂)ₙ–S(=O)₂OH |
| Sulfinic acids | –(CH₂)ₙ–S(=O)OH |
| Sulfonamides | –(CH₂)ₙ–S(=O)₂NH₂ |
| | –(CH₂)ₙ–NH–S(=O)₂CH₃ |
| Acyl sulfonamides | –(CH₂)ₙ–C(=O)NH–S(=O)₂CH₃ |
| Acyl sulfonamides | –(CH₂)ₙ–C(=O)NH–S(=O)₂NMe₂ |
| Sulfonylureas | –(CH₂)ₙ–NH–C(=O)NH–S(=O)₂CH₃ |
| Acylureas | –(CH₂)ₙ–NH–C(=O)NH–C(=O)CH₃ |
| Tetrazoles | –(CH₂)ₙ–(tetrazole) |
| Thiazolidine diones | –(CH₂)ₙ–(thiazolidine-2,4-dione) |
| Oxazolidine diones | –(CH₂)ₙ–(oxazolidine-2,4-dione) |
| Oxadiazol-5(4H)-ones | –(CH₂)ₙ–(1,2,4-oxadiazol-5(4H)-one) |

TABLE 2-continued
Other examples of R¹
| Generic Group | Non-limiting examples, n = 0-4 |
|---|---|
| Thiadiazol-5(4H)-ones | 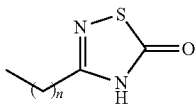 |
| Oxathiadiazole-2-oxides | 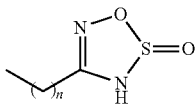 |
| Oxadiazole-5(4H)-thiones | 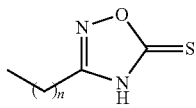 |
| Isoxazoles | 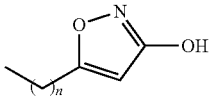 |
| Tetramic acids | 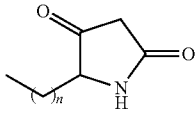 |
| Cyclopentane 1,3-diones | 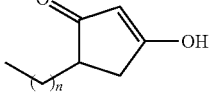 |
|  | 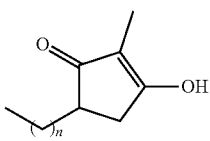 |
|  | 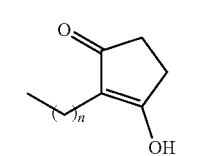 |
| Cyclopentane 1,2-diones | 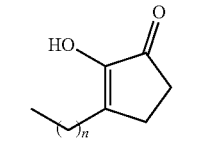 |
|  | 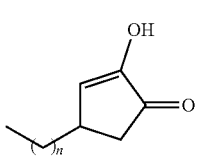 |
| Squaric acids | 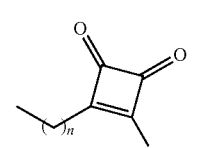 |
TABLE 2-continued
Other examples of R¹
| Generic Group | Non-limiting examples, n = 0-4 |
|---|---|
|  | 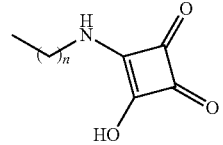 |
| Substituted phenols | 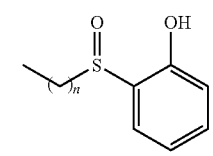 |
|  | 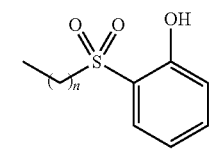 |
|  | 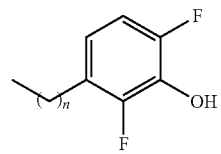 |
|  | 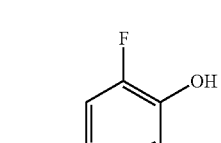 |
|  | |
| Heteroarenes | 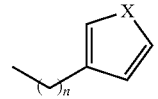 |
|  | X = O, NH, S |
|  | 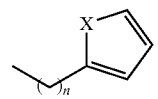 |
|  | X = O, NH, S |
|  | 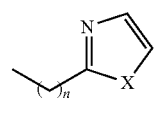 |
|  | X = O, S |

TABLE 2-continued

Other examples of $R^1$

| Generic Group | Non-limiting examples, n = 0-4 |
|---|---|
| Amidines | ![structure] |
| Hydroxyamides | ![structure] |
| Alkyl hydroxyamidines | ![structure] |

In at least certain non-limiting embodiments, the $R^2$ substituent of chemical structure I is selected from the group: H, F, Cl, Br, I, nitro ($NO_2$), alkyl (e.g., $CH_3$, $CH_2CH_3$, or any alkyl chain with 3-10 carbon atoms, branched or unbranched), alkoxy (e.g., $OCH_3$, $OCH_2CH_3$, or any alkyoxy chain with 3-10 carbon atoms, branched or unbranched), haloalkyl (e.g., $CH_2Cl$, $CHBr_2$, $CF_3$), haloalkoxyl, (e.g., $OCH_2Cl$, $OCHBr_2$, $OCF_3$), a 1, 2, 3, 4, 5, 6, 7, 8, 9, or 10 carbon haloalkyl having e.g., 1 to 3 halogen atoms, a 1, 2, 3, 4, 5, 6, 7, 8, 9, or 10 carbon haloalkoxyl having, e.g., 1 to 3 halogen atoms, cycloalkyl, halocycloalkyl, O-para-alkylbenzyl (e.g., where alkyl is methyl, ethyl, or propyl); O-para-alkyloxybenzyl (e.g., where alkyl is methyl, ethyl, or propyl); and O-para-halobenzyl (wherein halo=Cl, F, Br, or I).

In at least certain non-limiting embodiments, the $R^3$ substituent of ring "C" of chemical structure I is selected from the group: H, F, Cl, Br, I, $NO_2$, alkyl (e.g., $CH_3$, $CH_2CH_3$, or any alkyl chain with 3-10 carbon atoms, branched or unbranched), alkoxy (e.g., $OCH_3$, $OCH_2CH_3$, or any alkyoxy chain with 3-10 carbon atoms, branched or unbranched), haloalkyl (e.g., $CH_2Cl$, $CHBr_2$, $CF_3$), haloalkoxyl (e.g., $OCH_2Cl$, $OCHBr_2$, $OCF_3$), a 1, 2, 3, 4, 5, 6, 7, 8, 9, or 10 carbon haloalkyl having e.g., 1 to 3 halogen atoms, a 1, 2, 3, 4, 5, 6, 7, 8, 9, or 10 carbon haloalkoxyl having, e.g., 1 to 3 halogen atoms, cycloalkyl, and halocycloalkyl, wherein the "C" ring comprises one, two, three, four, or five of said $R^3$ substituents substituted in any combination of said $R^3$ substituents and arranged in any pattern in the "C" ring including ortho, meta, para, mono, di, tri, tetra, and pentasubstituted.

In at least non-limiting embodiments, each $R^4$ and $R^5$ substituent of chemical structure I can selected from the group: H, F, Cl, Br, I, $NO_2$, alkyl (e.g., branched or unbranched, $C_1$ to $C_{10}$), and haloalkyl (e.g., $CH_2Cl$, $CHBr_2$, $CF_3$). $R^4$ and $R^5$ may together consist of a double bonded O.

In at least certain non-limiting embodiments, $R^4$ and $R^5$ together form a cycloalkyl comprising two to 10 carbon atoms, or a halocycloalkyl comprising two to 10 carbon atoms and substituted with one or more halogen (Cl, F, Br, I) atoms.

In at least certain embodiments, when one of $R^4$ and $R^5$ is an alkyl or cycloalkyl (as defined herein), the other of $R^4$ and $R^5$ is H.

In at least certain non-limiting embodiments, each $R^6$ and $R^7$ substituent of chemical structure I can selected from the group: H, F, Cl, Br, I, alkyl (e.g., branched or unbranched, $C_1$ to $C_{10}$), and haloalkyl (e.g., $CH_2Cl$, $CHBr_2$, $CF_3$). $R^6$ and $R^7$ may together consist of a double bonded O.

In at least certain non-limiting embodiments, $R^6$ and $R^7$ together form a cycloalkyl comprising two to 10 carbon atoms, or a halocycloalkyl comprising two to 10 carbon atoms and substituted with one or more halogen (Cl, F, Br, I) atoms.

In at least certain embodiments, when one of $R^6$ and $R^7$ is an alkyl or cycloalkyl (as defined herein), the other of $R^6$ and $R^7$ is H.

As noted, in certain embodiments, rings A and/or B and/or C of chemical structure I may be a pyridine. Schemes 1-3 below show exemplary, non-limiting, synthetic pathways which can be used to form structures of the present disclosure which comprise rings A and/or B as pyridines:

Scheme 1

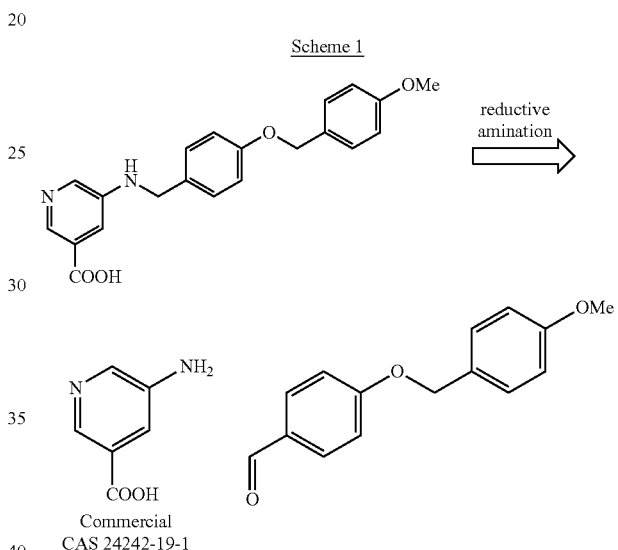

Scheme 2 and 3

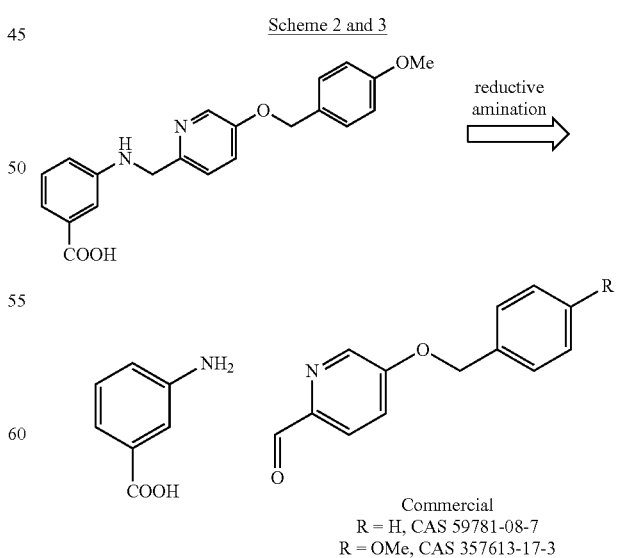

-continued

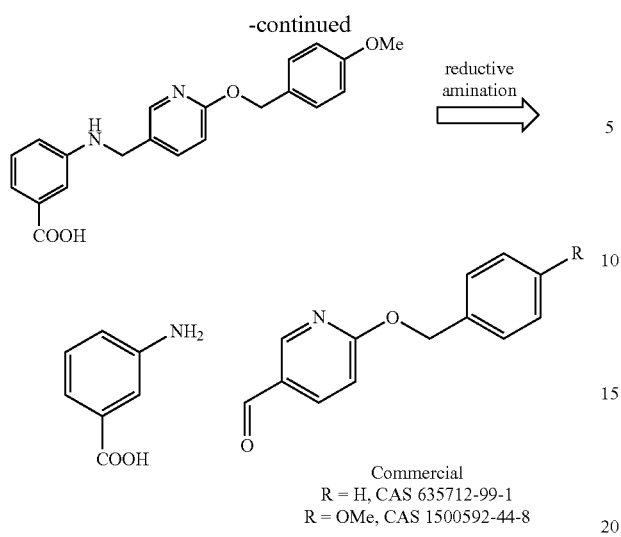

Commercial
R = H, CAS 635712-99-1
R = OMe, CAS 1500592-44-8

In at least certain alternate embodiments, the present disclosure includes active agent compositions and methods for treating ocular disorders and conditions, and particularly retinal conditions and disorders, which in certain non-limiting embodiments, include retinal inflammation, retinal neovascularization, retinal vascular leakage, retinopathy of prematurity (ROP), diabetic retinopathy (DR), age-related macular degeneration (e.g., wet AMD), and diabetic macular edema (DME) (or others disorders or conditions described elsewhere herein) using a compound having the chemical structure II:

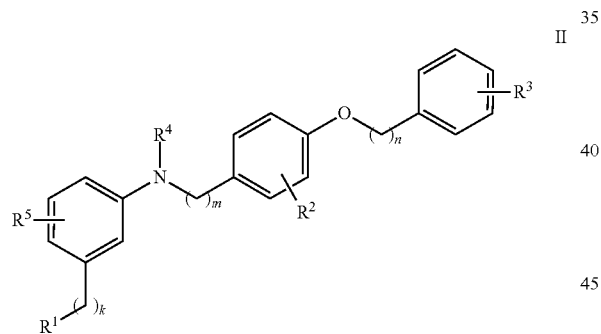

II wherein:
k is 0, 1, 2, 3, 4, 5, 6, 7, 8, 9, or 10 carbon atoms;
m is 0, 1, 2, 3, 4, or 5 carbon atoms;
n is 0, 1, 2, 3, 4, or 5 carbon atoms;
R2 is selected from the group: hydrogen (H), chlorine (Cl), fluorine (F), bromine (Br), iodine (I), nitro ($NO_2$), $CH_3$-, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^2$ comprises one, two, three, or four of said $R^2$ substituents substituted in any combination of said $R^2$ substituents and arranged in any pattern in the ring including ortho, meta, mono, di, tri, and tetrasubstituted;
$R^3$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^3$ comprises one, two, three, four, or five of said $R^3$ substituents substituted in any combination of said $R^3$ substituents and arranged in any pattern in the ring including ortho, meta, para, mono, di, tri, tetra, and pentasubstituted;
$R^4$ is selected from the group: H, alkyl, and acyl;
$R^5$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^5$ comprises one, two, three, or four of said $R^5$ substituents substituted in any combination of said $R^5$ substituents and arranged in any pattern in the ring including ortho, meta, para, mono, di, tri, and tetrasubstituted;
$R^1$ is selected from the group consisting of carboxylic acids, carboxylic acid isosteres, hydroxamic acids, hydroxamic esters, phosphonic acids, phosphinic acids, sulfonic acids, sulfinic acids, sulfonamides, acyl sulfonamides, sulfonylureas, acylureas, tetrazoles, thiazolidine diones, oxazolidine diones, oxadiazol-5(4H)-ones, thiadiazol-5(4H)-ones, oxathiadiazole-2-oxides, oxadiazol-5(4H)-thiones, isoxazoles, tetramic acids, cyclopentane 1,3-diones, cyclopentane 1,2-diones, squaric acids, substituted phenols, heteroarenes, amidines, hydroxyamides, alkyl hydroxyamidines, and

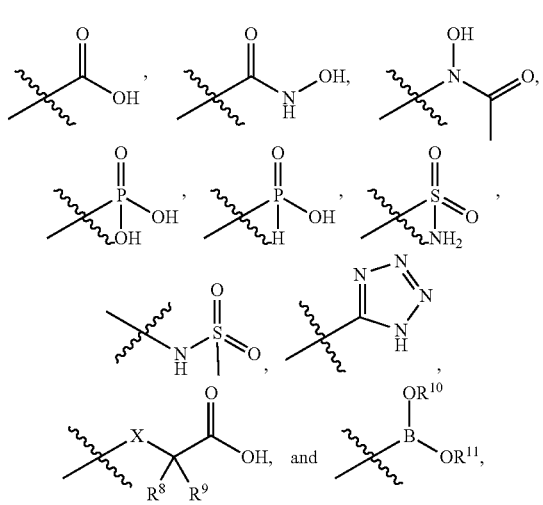

and salts thereof,
$R^8$ and $R^9$ are independently selected from the group consisting of H, F, Cl, Br, I, alkyl, alkoxy, and cycloalkyl comprising $R^8$ is linked to $R^9$;
$R^{10}$ and $R^{11}$ are independently selected from the group consisting of H, alkyl, and cycloalkyl wherein $R^{10}$ is linked to $R^{11}$); and
X is O, NH, S, or $CH_2$.

More particularly, in certain non-limiting embodiments of the present disclosure, examples of compounds having chemical structure II (compounds 9-14, 21-24, 26, and 28) are shown below:

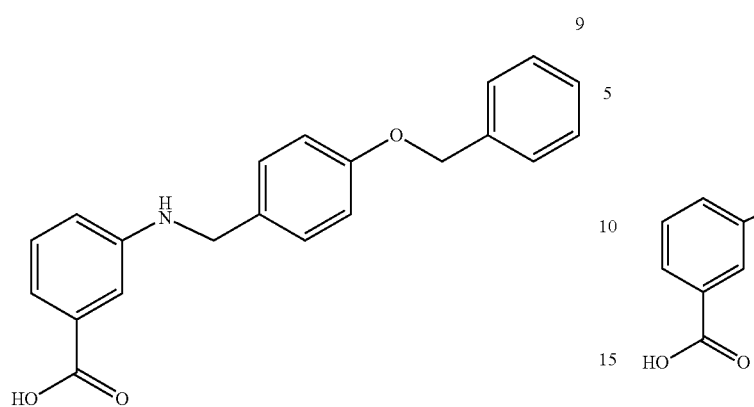
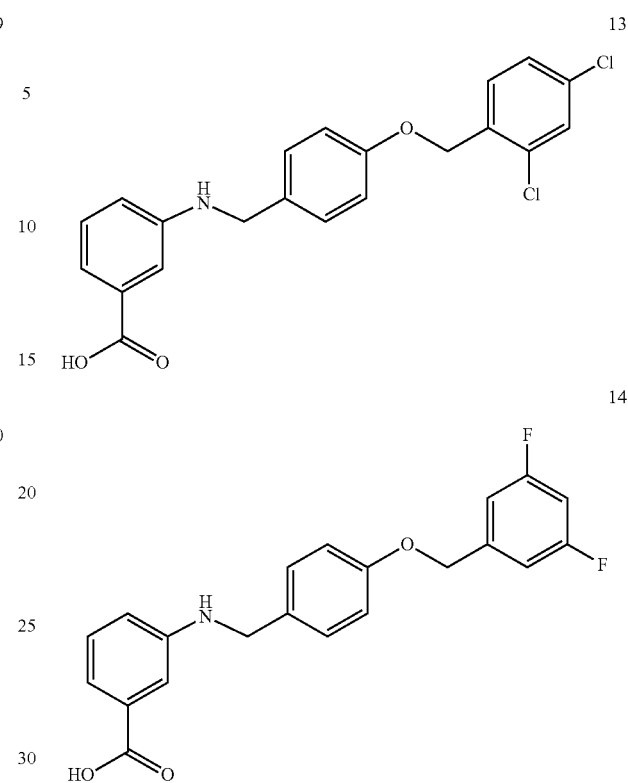
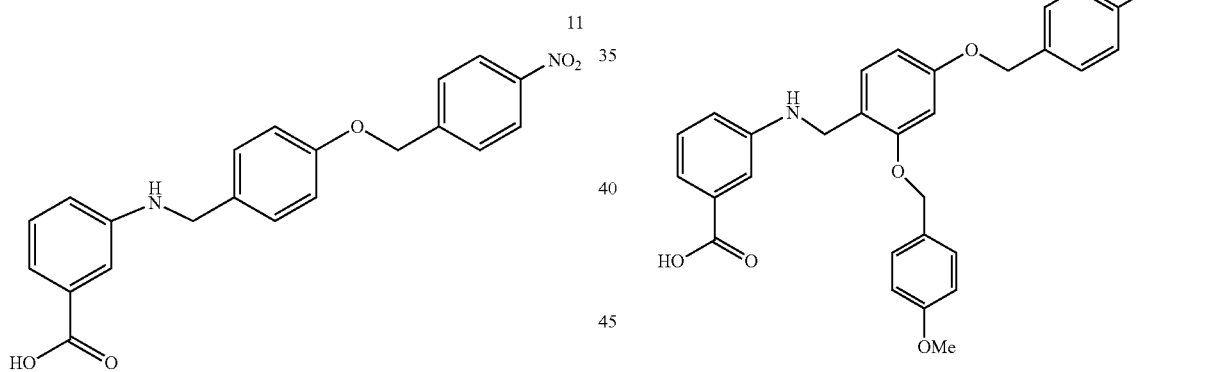
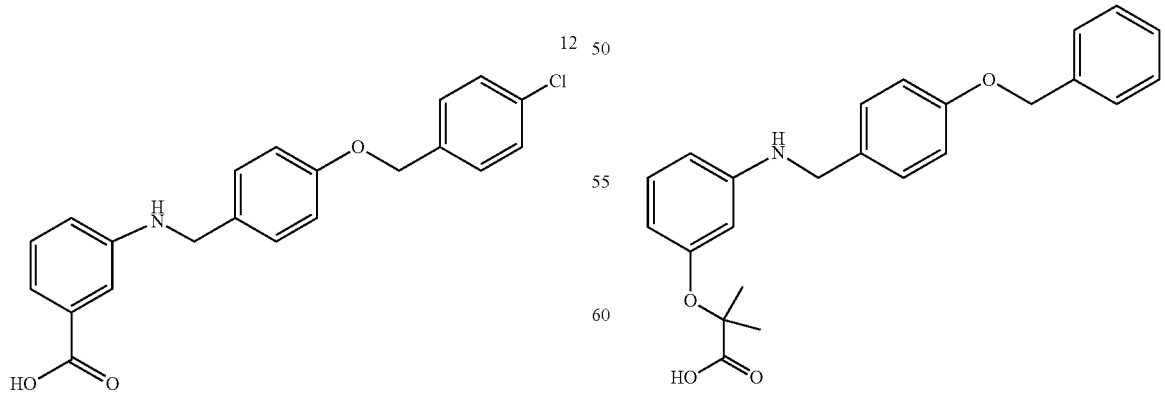

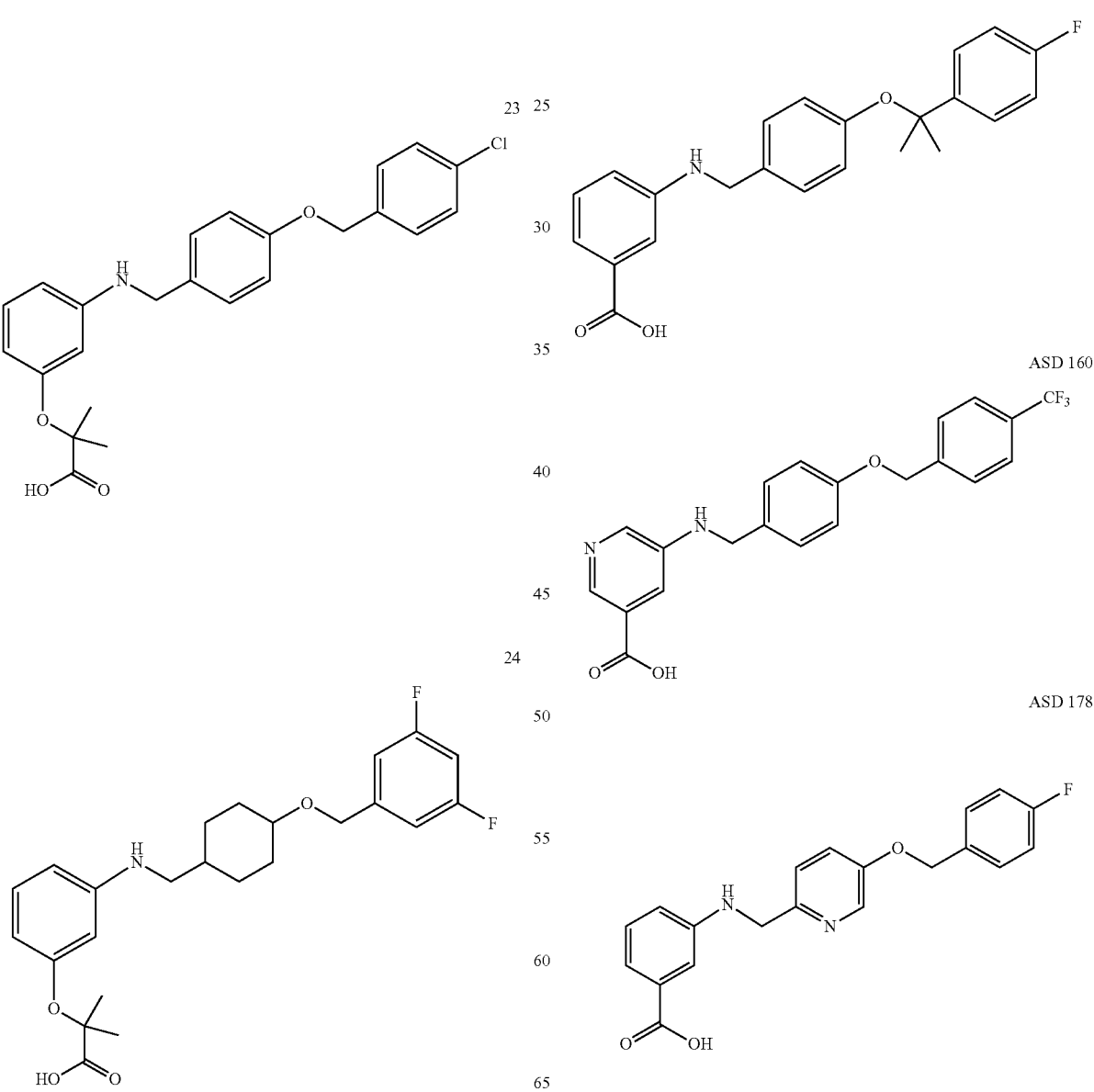

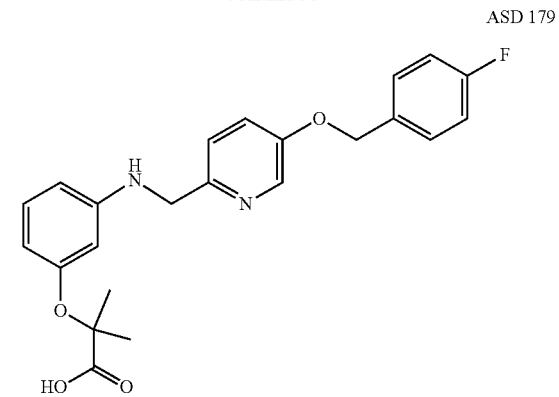

ASD 179

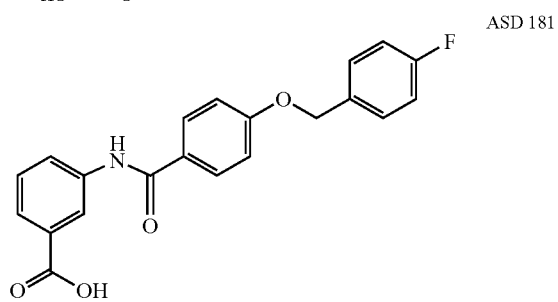

ASD 181

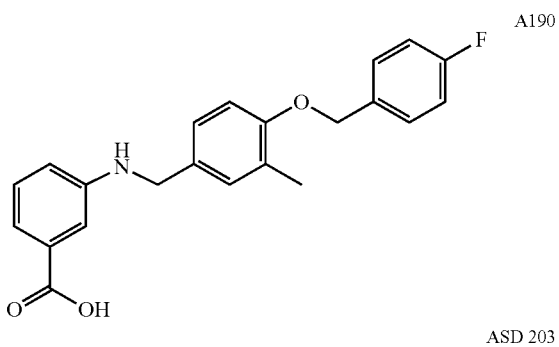

A190

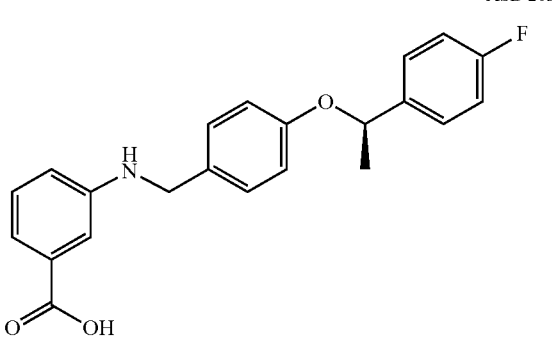

ASD 203

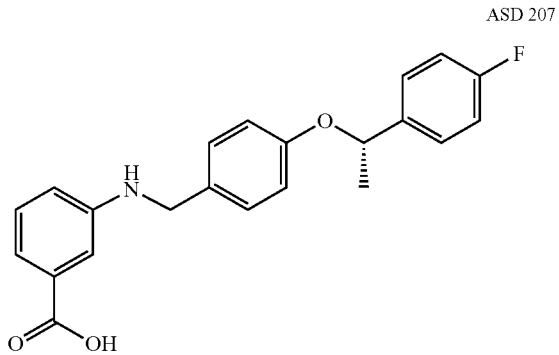

ASD 207

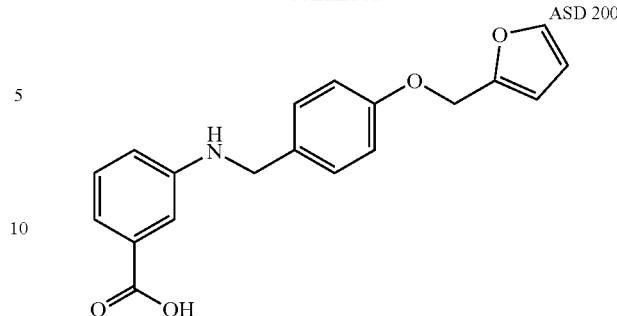

ASD 200

Compounds 9-14, 21-24, 26, and 28 are also numbered herein (e.g., in Tables 4 and 5) as 117, 91, 120, 122, 118, 119, 116, 114, 123, 121, 92, and 115, respectively. Compounds ASD152, ASD160, ASD178, ASD179, ASD181, ASD200, ASD203, and ASD207 are also referred to herein as compounds 152, 160, 178, 179, 181, 200, 203, and 207, respectively.

In certain embodiments, compounds (but not necessarily methods) of the present disclosure, may exclude compounds having chemical structure II wherein (1) $R^1$=COOH, and $R^2$-$R^5$=H, and (2) $R^1$=COOH, $R^3$=CH$_3$, and $R^2$, $R^4$, and $R^5$=H, such as the structures:

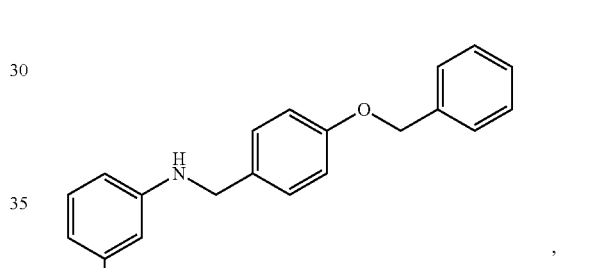

,

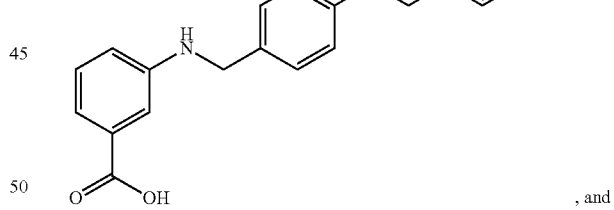

, and

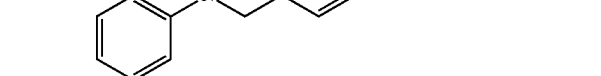

.

In at least certain alternate embodiments, the present disclosure includes active agent compositions and methods for treating ocular disorders and conditions, and particularly retinal conditions and disorders, which in certain non-limiting embodiments, include retinal inflammation, retinal neovascularization, retinal vascular leakage, retinopathy of prematurity (ROP), diabetic retinopathy (DR), age-related macular degeneration (e.g., wet AMD), and diabetic macular edema (DME) (or others disorders or conditions described elsewhere herein) using a compound having the chemical structure III:

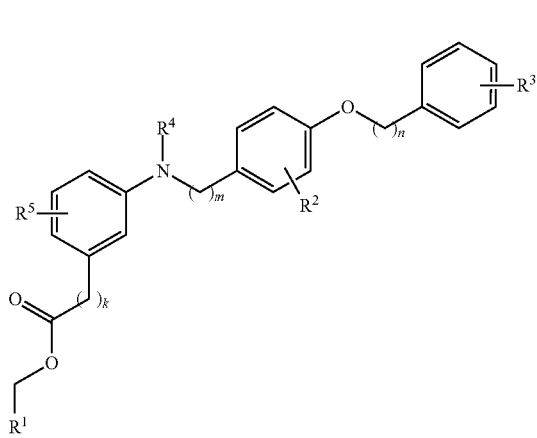

or salts or isomers thereof, wherein:
k is 0, 1, 2, 3, 4, 5, 6, 7, 8, 9, or 10 carbon atoms;
m is 0, 1, 2, 3, 4, or 5 carbon atoms;
n is 0, 1, 2, 3, 4, or 5 carbon atoms;
$R^1$ is selected from the group phosphate and phosphonate, and salts thereof;
$R^2$ is selected from the group: $CH_3$, hydrogen (H), chlorine (Cl), fluorine (F), bromine (Br), iodine (I), nitro ($NO_2$), $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^2$ comprises one, two, three, or four of said $R^2$ substituents substituted in any combination of said $R^2$ substituents and arranged in any pattern in the ring including ortho, meta, mono, di, tri, and tetrasubstituted;
$R^3$ is selected from the group: F, H, Cl, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^3$ comprises one, two, three, four, or five of said $R^3$ substituents substituted in any combination of said $R^3$ substituents and arranged in any pattern in the ring including ortho, meta, para, mono, di, tri, tetra, and pentasubstituted;
$R^4$ is selected from the group: H, alkyl, and acyl; and
$R^5$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^5$ comprises one, two, three, or four of said $R^5$ substituents substituted in any combination of said $R^5$ substituents and arranged in any pattern in the ring including ortho, meta, para, mono, di, tri, and tetrasubstituted.

In a particular embodiment, the compound has the chemical structure IIIA:

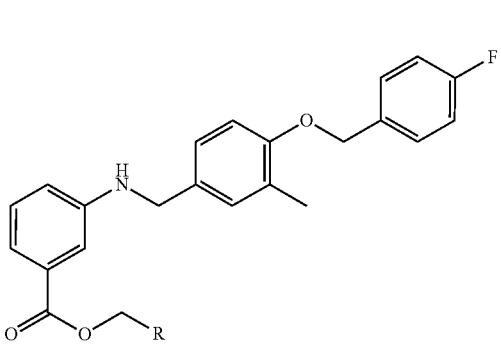

wherein R is is selected from the group phosphate and phosphonate, and salts thereof.

In one embodiment, the compound is a monosodium salt designated by the identifier ZH-2021-162 and has the following structure:

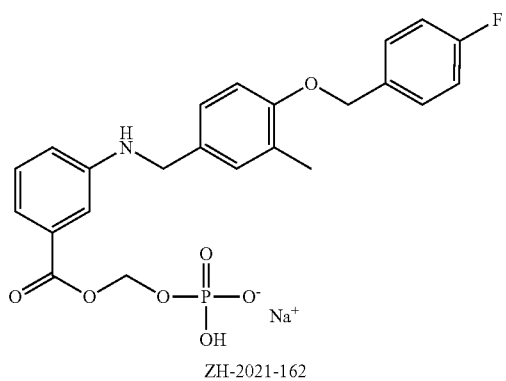 [SMILES: Cc1cc(CNc2cccc(C(=O)OCOP(=O)([O-])O)c2)ccc1OCc1ccc(F)cc1 ; [Na+]]

ZH-2021-162

In one embodiment, the compound is a monotris salt designated by the identifier ZH-2021-164 and has the following structure:

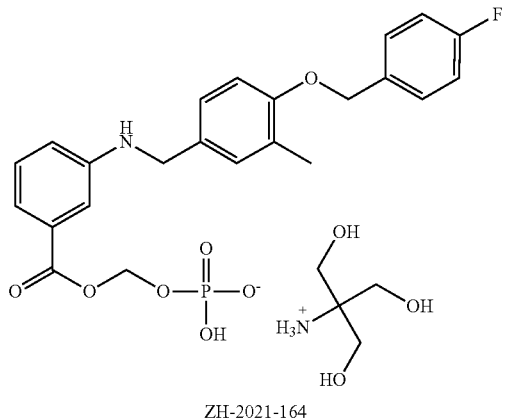 [SMILES: Cc1cc(CNc2cccc(C(=O)OCOP(=O)([O-])O)c2)ccc1OCc1ccc(F)cc1 ; NC(CO)(CO)CO]

ZH-2021-164

Exemplary salts of the phosphate and phosphonate compounds include but are not limited to sodium, potassium, calcium, magnesium, ammonium, iron, quaternaryalkylammonium, quaternaryarylammonium. The cation may be a metal ion, such as a alkali metal ion (e.g., sodium, potassium, lithium), an alkaline earth metal ion (e.g., magnesium, calcium, barium), or an aluminum ion. The cation may be an ammonium ion, a quaternary alkylammonium, a quaternary arylammonium, or an ammonium ion derived from an organic base, such as but not limited to ethanolamine, diethanolamine, triethanolamine, N-methylglucamine, morpholine, piperidine, pyridine, dimethylamine, diethylamine, trimethylamine, triethylamine, isopropylamine, 2-ethylamino ethanol, histidine, lysine, procaine, and Tris (2-amino-2-(hydroxymethyl)propane-1,3-diol).

Comparative solubilities of various compounds are shown in Table 3.

TABLE 3

Solubilities of various compounds

| Compound ID | PBS Solubility pH 7.4 (μM) | $H_2O$ Solubility (μM) |
|---|---|---|
| 190 | 270 | 27 |
| Fenofibrate | 0.3 | 0.3 |
| Fenofibric acid | 278 | 93 |
| ZH-2021-162 (monosodium salt) | 292 | 318 |
| ZH-2021-164 (monotris salt) | 316 | 284 |

Certain non-limiting embodiments of the present disclosure include pharmaceutical compositions that include at least one pharmaceutically acceptable carrier in combination with one or more compounds described herein that are agonists of PPARα and have anti-inflammatory and anti-angiogenic activities in the eye, particularly in the retina and macula. Particular non-limiting examples of pharmaceutical (therapeutic) compositions formulated in accordance with the present disclosure include: (a) a pharmaceutical composition comprising a PPARα agonist in combination with at least one pharmaceutically acceptable carrier, such as a polymer; and (b) a PPARα agonist in combination with at least one other therapeutically active agent, and at least one pharmaceutically acceptable carrier, such as a polymer.

As noted above, the active agents of the present disclosure can be used to treat diseases and conditions associated with retinal endothelial dysfunction, angiogenesis and inflammation, such as, for example, DR and AMD (e.g., wet AMD), retinal inflammation, retinal neovascularization (NV), retinal vascular leakage, retinopathy of prematurity (ROP), and diabetic macular edema (DME).

Suitable carriers, vehicles, excipients, diluents, and other components that may be included in the formulation are described, for example, in *Remington: The Science and Practice of Pharmacy*, 21$^{st}$ Ed. and 22$^{nd}$ Ed. The term "pharmaceutically acceptable" means that the carrier is a non-toxic material that does not interfere with the effectiveness of the biological activity of the active agent. The characteristics of the carrier will depend on various factors, including but not limited to, the route of administration.

The active agents disclosed herein (i.e., the phosphate and/or phosphonate compounds) can be formulated into compositions for delivery to a subject. The composition can be administered alone and/or mixed with a pharmaceutically acceptable vehicle or excipient. Suitable vehicles are, for example (but not by way of limitation), water, saline, dextrose, glycerol, ethanol, or the like, and combinations thereof. In addition, the vehicle can contain minor amounts of auxiliary substances such as (but not limited to) wetting or emulsifying agents, pH buffering agents, or adjuvants. The compositions of the present disclosure can also include ancillary substances, including other pharmacological agents.

The active agent can be delivered alone or as pharmaceutical compositions by any means known in the art, such as (but not limited to) systemically, regionally, or locally; by intra-arterial, intrathecal (IT), intravenous (IV), parenteral, intra-pleural cavity, topical, oral, transdermal delivery, or local administration, as ocular, subcutaneous, intra-tracheal (e.g., by aerosol) or transmucosal (e.g., buccal, bladder, vaginal, uterine, rectal, nasal mucosa), subcutaneous, intracranial, intraocular, intracerebral, intracavitary, intraperitoneal, intranasal, intralymphatic, or intramuscular. Intravenous administration can be, for example (but not by way of limitation), by infusion over a period such as (but not limited to) 30-90 min or by a single bolus injection. As noted above, the compositions can be formulated into compositions in either neutral or salt forms.

Compositions for therapies can be administered in a single dose treatment or in multiple dose treatments on a schedule and over a time period appropriate to the age, weight, and condition of the subject, the particular composition used, and the route of administration. In one non-limiting embodiment, a single dose of the composition according to the disclosure is administered. In other non-limiting embodiments, multiple doses are administered. The frequency of administration can vary depending on any of a variety of factors, e.g., severity of the symptoms, or whether the composition is used for prophylactic or curative purposes. For example, in certain non-limiting embodiments, the composition is administered once per month, twice per month, three times per month, every other week, once per week, twice per week, three times per week, four times per week, five times per week, six times per week, every other day, daily, twice a day, or three times a day. The duration of treatment (i.e., the period of time over which the composition is administered) can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) to form a pharmacological composition. Pharmaceutically acceptable carriers can contain a physiologically acceptable compound that acts to, for example but not by way of limitation) stabilize or increase or decrease the absorption or clearance rates of the pharmaceutical compositions. Physiologically acceptable compounds can include, for example but not by way of limitation: carbohydrates, such as glucose, sucrose, or dextrans; antioxidants, such as ascorbic acid or glutathione; chelating agents; low molecular weight proteins; detergents; liposomal carriers; excipients; or other stabilizers and/or buffers. Other physiologically acceptable compounds include (but are not limited to) wetting agents, emulsifying agents, dispersing agents, or preservatives.

When administered orally, the present compositions may be protected from digestion. This can be accomplished either by combining the active agent with a composition to render it resistant to acidic and enzymatic hydrolysis or by packaging the active agent in an appropriately resistant carrier such as (but not limited to) a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical transdermal administration, the active agents are formulated into ointments, creams, salves, powders, and gels. Transdermal delivery systems can also include (for example but not by way of limitation) patches. The present compositions can also be administered in sustained delivery or sustained release mechanisms. For example, biodegradeable microspheres or capsules or other biodegradeable polymer configurations capable of sustained delivery can be used.

In one aspect, the compositions are prepared with carriers that will protect the active agent against rapid elimination from the body, such as (but not limited to) a controlled release formulation, including implants and microencapsulated delivery systems. Biodegradable, biocompatible polymers can be used, such as (but not limited to) ethylene vinyl acetate, polyanhydrides, polyglycolic acid, collagen, polyorthoesters, and polylactic acid. Methods for preparation of such formulations will be apparent to those skilled in the art.

The active agent in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active compound is combined in a mixture with one or more pharmaceutically suitable excipients. Sterile phosphate-buffered saline is one non-limiting example of a pharmaceutically suitable excipient.

In parenteral administration, the compositions will be formulated in a unit dosage injectable form such as (but not limited to) a solution, suspension, or emulsion, in association with a pharmaceutically acceptable excipient. Such excipients are inherently nontoxic and nontherapeutic. Non-limiting examples of such excipients include saline, Ringer's solution, dextrose solution, and Hanks' solution. Non-aqueous excipients such as (but not limited to) fixed oils and ethyl oleate may also be used. An alternative non-limiting excipient is 5% dextrose in saline. The excipient may contain minor amounts of additives such as (but not limited to) substances that enhance isotonicity and chemical stability, including buffers and preservatives.

Formulated compositions comprising the active agent can be used (for example but not by way of limitation) for subcutaneous, intramuscular, or transdermal administration. Compositions can be presented in unit dosage form, e.g., in ampoules or in multi-dose containers, with an added preservative. Compositions can also take such forms as suspensions, solutions, or emulsions in oily or aqueous vehicles, and can contain formulatory agents such as suspending, stabilizing, and/or dispersing agents. Alternatively, the compositions can be in powder form for constitution with a suitable vehicle, e.g., sterile pyrogen-free water, before use.

In certain non-limiting embodiments, pharmaceutical compositions for parenteral administration are sterile, substantially isotonic, and manufactured under GMP conditions. Pharmaceutical compositions can be provided in unit dosage form (i.e., the dosage for a single administration). Pharmaceutical compositions can be formulated using one or more physiologically acceptable carriers, diluents, excipients, or auxiliaries. The formulation depends on the route of administration chosen. For injection, the active agent can be formulated in aqueous solutions, such as (but not limited to) in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, the active agent can be in lyophilized form for constitution with a suitable vehicle, e.g., sterile pyrogen-free water, before use.

Some non-limiting embodiments provided herein include kits. In some non-limiting embodiments, a kit can include a quantity of an active agent as described or otherwise contemplated herein, In some non-limiting embodiments, the active agent is lyophilized. In some non-limiting embodiments, the active agent is in aqueous solution, or other carrier as described herein. In some non-limiting embodiments, the kit includes a pharmaceutical carrier for administration of the active agent. Certain non-limiting embodiments of the present disclosure include kits containing components suitable for treatments or diagnosis. Exemplary kits may contain at least one active agent. A device capable of delivering the kit components by injection, for example, a syringe for subcutaneous injection, may be included in some non-limiting embodiments. Where transdermal administration is used, a delivery device such as hollow microneedle delivery device may be included in the kit in some non-limiting embodiments. Exemplary transdermal delivery devices are known in the art, such as (but not limited to) a hollow Microstructured Transdermal System (e.g., 3M Corp.), and any such known device may be used. The kit components may be packaged together or separated into two or more containers. In some non-limiting embodiments, the containers may be vials that contain sterile, lyophilized formulations of a composition that are suitable for reconstitution. A kit may also contain one or more buffers suitable for reconstitution and/or dilution of other reagents. Alternatively, the active agent may be delivered and stored as a liquid formulation. Other containers that may be used include, but are not limited to, a pouch, tray, box, tube, or the like. Kit components may be packaged and maintained sterilely within the containers. Another component that can be included is instructions for the use of the kit for treatment.

The term "coadministration" refers to administration of two or more active agents, e.g., a PPARα agonist, and another active agent. The timing of coadministration depends in part of the combination and compositions administered and can include administration at the same time, just prior to, or just after the administration of one or more additional therapies Coadministration is meant to include simultaneous or sequential administration of the compound and/or composition individually or in combination. Thus, the preparations can also be combined, when desired, with other active substances (e.g., to reduce metabolic degradation).

For inhalation, the present compositions can be delivered using any system known in the art, including (but not limited to) dry powder aerosols, liquids delivery systems, air jet nebulizers, propellant systems, and the like. For example (but not by way of limitation), the pharmaceutical formulation can be administered in the form of an aerosol or mist. For aerosol administration, the formulation can be supplied in finely divided form along with a surfactant and propellant.

In another aspect, the device for delivering the formulation to respiratory tissue is an inhaler in which the formulation vaporizes. Other liquid delivery systems include (for example but not by way of limitation) air jet nebulizers.

The active agents of the present disclosure may be present in the pharmaceutical compositions at any concentration that allows the pharmaceutical composition to function in accordance with the present disclosure; for example, but not by way of limitation, the compound(s) may be present in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Exemplary, non-limiting ranges for a therapeutically or prophylactically effective amount of the active agent, include a range of from about 0.001 mg/kg of the subject's body weight to about 500 mg/kg of the subject's body weight, such as but not limited to a range of from about 0.01 mg/kg to about 250 mg/kg, a range of from about 0.1 mg/kg to about 100 mg/kg, a range of from about 0.1 mg/kg to about 50 mg/kg, a range of from about 1 mg/kg to about 30 mg/kg, a range of from about 1 mg/kg to about 25 mg/kg, a range of from about 2 mg/kg to about 30 mg/kg, a range of from about 2 mg/kg to about 20 mg/kg, a range of from about 2 mg/kg to about 15 mg/kg, a range of from about 2 mg/kg to about 12 mg/kg, a range of from about 2 mg/kg to about 10 mg/kg, a range of from about 3 mg/kg to about 30 mg/kg, a range of from about 3 mg/kg to about 20 mg/kg, a range of from about 3 mg/kg to about 15 mg/kg, a range of from about 3 mg/kg to about 12 mg/kg, or a range of from about 3 mg/kg to about 10 mg/kg, or a range of from about 10 mg to about 1500 mg as a fixed dosage.

The composition is formulated to contain an effective amount of the active agent, wherein the amount depends on the subject to be treated and the severity of the condition of the subject. In certain non-limiting embodiments, the active agents may be administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 40 µg to about 300 µg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, or from about 1 mg to about 2 mg. The specific dose level for any particular subject depends upon a variety of factors, including (but not limited to) the activity of the specific active agent, the age, body weight, general health, sex, diet, time of administration, route of administration, and rate of excretion, the drug combination, and the severity of the disease in the subject undergoing therapy.

In some non-limiting embodiments, the amount of an active agent is in a concentration of about 1 nM, about 5 nM, about 10 nM, about 25 nM, about 50 nM, about 75 nM, about 100 nM, about 150 nM, about 200 nM, about 250 nM, about 300 nM, about 350 nM, about 400 nM, about 500 nM, about 550 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 60 µM, about 70 µM, about 75 µM, about 80 µM, about 90 µM, about 100 µM, about 125 µM, about 150 µM, about 175 µM, about 200 µM, about 250 µM, about 300 µM, about 350 µM, about 400 µM, about 500 µM, about 600 µM, about 700 µM, about 750 µM, about 800 µM, about 900 µM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 500 mM, about 600 mM, about 700 mM, about 800 mM, about 900 mM, about 1000 mM, about 1 M, about 1.1 M, about 1.2 M, about 1.3 M, about 1.4 M, about 1.5 M, about 1.6 M, about 1.7 M, about 1.8 M, about 1.9 M, about 2 M, about 3 M, about 4 M, about 5 M, about 6 M, about 7 M, about 8 M, about 9 M, about 10 M, about 15 M, about 20 M, about 25 M, about 30 M, about 35 M, about 40 M, about 45 M, about 50 M, about 75 M, about 100 M, or any range in between any two of the aforementioned concentrations, including said two concentrations as endpoints of the range, or any number in between any two of the aforementioned concentrations.

The dosage of an administered active agent for humans will vary depending upon factors such as (but not limited to) the patient's age, weight, height, sex, general medical condition, and previous medical history. In certain non-limiting embodiments, the recipient is provided with a dosage of the active agent(s) that is in the range of from about 1 mg to about 1000 mg as a single infusion or single or multiple injections, although a lower or higher dosage also may be administered. In certain non-limiting embodiments, the dosage may be in the range of from about 25 mg to about 100 mg per square meter ($m^2$) of body surface area for a typical adult, although a lower or higher dosage also may be administered. Non-limiting examples of dosages that may be administered to a human subject further include 1 to 500 mg, 1 to 70 mg, or 1 to 20 mg, although higher or lower doses may be used. Dosages may be repeated as needed, for example (but not by way of limitation), once per week for 4-10 weeks, once per week for 8 weeks, or once per week for 4 weeks. It may also be given less frequently, such as (but not limited to) every other week for several months, or more frequently, such as twice weekly or by continuous infusion.

The compositions may be administered in solution. The formulation thereof may be in a solution having a suitable pharmaceutically acceptable buffer, such as (but not limited to) phosphate, Tris (hydroxymethyl) aminomethane-HCl, or citrate, and the like. Buffer concentrations may be in the range of 1 to 100 mM. The formulated solution may also contain a salt, such as (but not limited to) sodium chloride or potassium chloride in a concentration of 50 to 150 mM. An effective amount of a stabilizing agent such as (but not limited to) mannitol, trehalose, sorbitol, glycerol, albumin, a globulin, a detergent, a gelatin, a protamine, or a salt of protamine may also be included.

The number of dosages administered depends on the severity of the condition and the response to therapy (e.g., whether presenting acute or chronic symptoms) Treatment can be repeated for recurrence of an acute disorder or acute exacerbation. For chronic disorders, the active agent can be administered at regular intervals, such as (but not limited to) weekly, fortnightly, monthly, quarterly, every six months for at least 1, 5, or 10 years, or for the life of the patient if the condition is chronic.

Other embodiments of the pharmaceutical compositions of the present disclosure may include the incorporation or entrapment of the active agents in various types of drug delivery systems that function to provide targeted delivery, controlled release, and/or increased half-life to the active agents. For example, but not by way of limitation, it is possible to entrap the active agents in microcapsules prepared by coacervation techniques or by interfacial polymerization (for example, hydroxymethylcellulose or gelatin-microcapsules and poly-(methylmethacylate) microcapsules, respectively). It is also possible to entrap the active agents in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the active agents of the present disclosure may be incorporated into particles of one or more polymeric materials, as this type of incorporation can be useful in controlling the duration of action of the active agents by allowing for controlled release from the preparations, thus increasing the half-life thereof. Non-limiting examples of polymeric materials that may be utilized in this manner include polyesters, polyamides, polyamino acids, hydrogels, poly(lactic acid-glycolic acid), poly(lactic acid), ethylene vinylacetate copolymers, copolymer micelles of, for example, PEG and poly(l-aspartamide), and combinations thereof.

In certain non-limiting embodiments, the pharmaceutical composition containing the active agents may be in the form of an ophthalmic composition for topical application to an eye of a subject. The term "ophthalmic composition" as used herein will be understood to refer to any composition specifically formulated for direct and local administration to an eye of a patient. Said composition may be formulated for topical administration to the eye or for injection into the eye (i.e., intravitreal or intraocular injection). The ophthalmic composition may be provided in any formulation that allows for local administration thereof to the eye and allows the active agents to function in accordance with the present disclosure. For example, but not by way of limitation, the ophthalmic composition may be provided in the form of a solution, drops, a mist/spray, plasters and pressure sensitive adhesives, an ointment, a lotion, a cream, a gel, lyophilized/spray-dried forms, and the like. In one particular non-limiting embodiment, the ophthalmic composition is provided in a form for topical application, such as but not limited to, an eyedrop formulation. The ophthalmic compositions of the present disclosure may vary according to the particular active agent(s) used, the desired drug release profile, the condition being treated, and/or the medical history of the patient. In addition, the ophthalmic compositions of the present disclosure may be designed to provide delayed, controlled, extended, and/or sustained release using formulation techniques which are well known in the art, and as explained elsewhere herein.

The pharmaceutical compositions described or otherwise contemplated herein may further comprise at least one delivery agent that assists in delivery of the active agents to a desired site of delivery; for example but not by way of limitation, at least one delivery agent may be included in an ophthalmic composition to assist in the penetration of a surface of an eye; in certain embodiments, the delivery agent may assist in delivery to a retina of the eye. For example, in order for a topical application to be effective, the composition may need to be able to penetrate the surface of the eye so that it can travel to the desired tissue. This may include penetrating the conjunctiva and/or the cornea.

When the ophthalmic composition containing the active agent(s) is formulated for administration by injection, the composition may be in the form of a pyrogen-free, aqueous solution or suspension. The preparation of such solutions, having due regard to pH, isotonicity, stability, and the like, is well within the skill of one of ordinary skill in the art. Suitable carriers include, but are not limited to, biocompatible and pharmaceutically acceptable phosphate buffered saline solutions, which are particularly isotonic. For example, but not by way of limitation, a particular ophthalmic composition may contain, in addition to the therapeutic compound(s), an isotonic vehicle such as Sodium Chloride Injection, Ringer's Injection, Dextrose Injection, Dextrose and Sodium Chloride Injection, Lactated Ringer's Injection, or other vehicles as known in the art. In general, the material for intravenous injection in humans should conform to regulations established by the US Food and Drug Administration, which are available to those in the field.

In addition to the ophthalmic administrations discussed in detail herein above, the therapeutic compositions of the present disclosure may be formulated for administration by any other method known or otherwise contemplated in the art, as long as the route of administration allows for delivery of the active agent(s) so that the compounds can function in accordance with the present disclosure, i.e., as a PPARα agonist. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically (e.g., ophthalmically) acceptable carrier, vehicle, diluent, excipient, or other agent for mixing with the active agent(s) for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition(s). When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of active material calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent(s) may sometimes be a minor component (from about 0.1 to about 50% by weight, such as but not limited to, from about 1 to about 40% by weight) with the remainder being various vehicles or carriers and processing aids helpful for forming the desired dosing form.

As is evident from the above, the active agent(s) of the present disclosure function as PPARα agonists for the treatment, inhibition, mitigation, and/or prevention of degenerative retinal disorders. Thus, certain non-limiting embodiments of the present disclosure include methods of treating, inhibiting, and/or reducing the occurrence of retinal degeneration due to retinal inflammation and neovascularization. One particular but non-limiting embodiment includes a method of treating, inhibiting, and/or reducing the occurrence of one or more pathologic ocular conditions associated with reduced PPARα activity in a subject. In the method, one or more of any of the active agent(s) or pharmaceutical compositions described or otherwise contemplated herein is administered to a subject (such as, but not limited to, a mammal) that is experiencing retinal or macular degeneration or that is predisposed to developing retinal or macular degeneration, or other ocular condition or disorder. The active agent(s) or pharmaceutical composition (s) is administered to the subject in an amount effective to have PPARα agonistic activity in the retina of at least one eye of the subject.

The pathologic ocular condition may be any of the conditions described herein, and the pathologic ocular condition may be characterized by retinal and/or macular degeneration. In one embodiment, the pharmaceutical composition may be administered topically to an eye of the subject (such as, but not limited to, as an eyedrop). In an alternative embodiment, the pharmaceutical composition may be administered by ocular injection, or systemically.

The amount of the active agent(s) that is effective in the treatment described herein can be determined by the attending diagnostician, as one of ordinary skill in the art, by the use of conventional techniques and by observing results obtained under analogous circumstances. For example, in one non-limiting embodiment of a treatment, in determining the therapeutically effective dose, a number of factors may be considered by the attending diagnostician, including, but not limited to: the species of the subject; its size, age, and general health; the specific disease and/or condition involved; the degree, involvement, and/or severity of the disease and/or condition; the response of the individual subject; the particular active agent(s) or other therapeutic compound(s) administered; the mode of administration; the bioavailability characteristics of the preparation administered; the dose regimen selected; the use of concomitant medication; and other relevant circumstances. A therapeutically effective amount of a pharmaceutical composition of the present disclosure also refers to an amount of the active agent(s) which is effective in controlling and/or reducing or amelieorating the disease and/or condition.

For example, but not by way of limitation, the therapeutically effective amount of a active agent(s) used in the present disclosure will generally contain sufficient active ingredient to deliver in a range of from about 0.01 µg/kg to about 10 mg/kg (weight of active ingredient/body weight of patient). For example, but not by way of limitation, the composition will deliver about 0.1 µg/kg to about 5 mg/kg, and more particularly about 1 µg/kg to about 1 mg/kg.

Practice of the method of the present disclosure may include administering to a subject a therapeutically effective amount of the pharmaceutical composition (containing the active agent(s)) in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

Experimental

The anti-inflammatory and anti-angiogenic activities of certain active agent(s) disclosed herein were investigated. Prior to the present work, none of the compounds described herein have been reported to have PPARα agonist activity, except 7-chloro-8-methyl-2-phenylquinoline-4-carboxylic acid (designated herein as Y-0452), fenofibrate, GW409544, and GW590735, shown directly below:

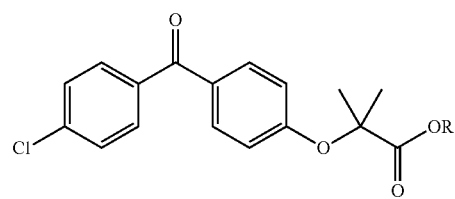

Fenofibrate, R = i-pr
Fenofibric Acid, R = OH

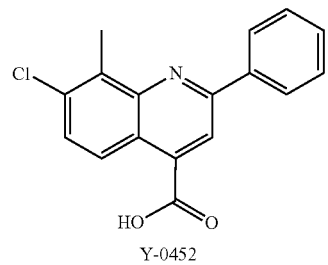

Y-0452

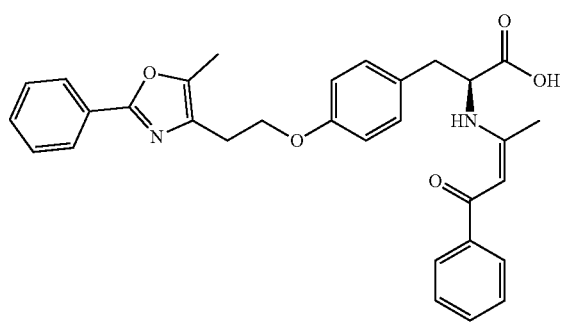

GW409544

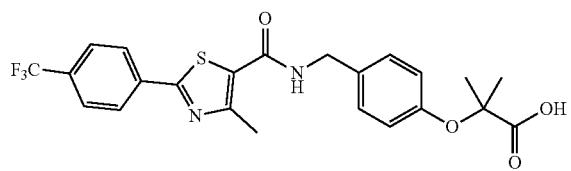

GW590735

A series of derivatives bearing some structural similarity to Y-0452 were evaluated for PPARα agonism. Compounds 9-14 and 21-24 were designed with an aim to fill a hydrophobic binding pocket in the PPARα more efficiently.

Derivatives 9-14 were synthesized as shown in Scheme 4. Commercially available 4-hydroxybenzaldehyde was coupled with various benzyl bromides 3-8 to afford benzaldehydes 3a-8a. Treatment of 3a-8a with 3-aminobenzoic acid produced the respective imines in situ, which were then reduced upon the addition of sodium triacetoxyborohydride to provide 9-14 in an unoptimized 40-82% yield.

Scheme 4. Synthesis of benzoic acid derivatives 9-14. Reagents and conditions: (a) benzyl bromide (i.e., 3-8), K₂CO₃, DMF, 80° C., 12 h; (b) 3-aminobenzoic acid, toluene, 155° C., 2 h; sodium triacetoxyborohydride, AcOH, THF, 0° C. to 25° C., 12 h.

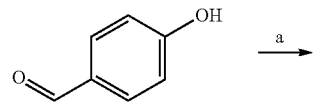

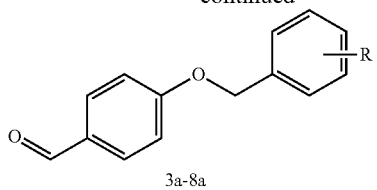

3a-8a

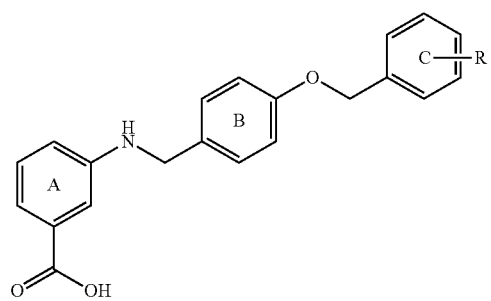

9, R = H
10, R = p-OMe
11, R = p-NO₂
12, R = p-Cl
13, R = o,p-dichloro
14, R = m-difluoro

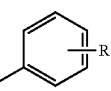

3, R = H
4, R = p-OMe
5, R = p-NO₂
6, R = p-Cl
7, R = o,p-dichloro
8, R = m-difluoro In addition to the benzoic acids derivatives 9-14, we wanted to incorporate the classical "head-group" of fenofibrate an aim to improve potency and instill selectivity for PPARα over other isoforms. The preparation of these analogs is depicted in Scheme 5. Commercially available 3-nitrophenol was coupled with ethyl α-bromoisobutyrate to afford 15, which was then reduced to the corresponding aniline (16) under catalytic hydrogenation conditions (H₂ and Pd/C in ethanol). Treatment of 16 with 3a, 4a, 6a, or 8a followed by reduction with sodium triacetoxyborohydride yielded 17-20, respectively. Hydrolysis of the pendant ester gave the desired products 21-24 in an unoptimized 46-88% yield.

Scheme 5. Synthesis of 21-24. Reagents and conditions: (a) ethyl α-bromoisobutyrate, K₂CO₃, DMF, 80° C., 12 h; (b) H₂, Pd/C, ethanol, 12 h; (c) aldehyde (i.e., 3a, 4a, 6a, or 8a), toluene, 155° C., 2h; sodium triacetoxyborohydride, AcOH, THF, 0° C. to 25° C., 12 h; (d) LiOH·H₂O, THF/MeOH/H₂O, 12 h.

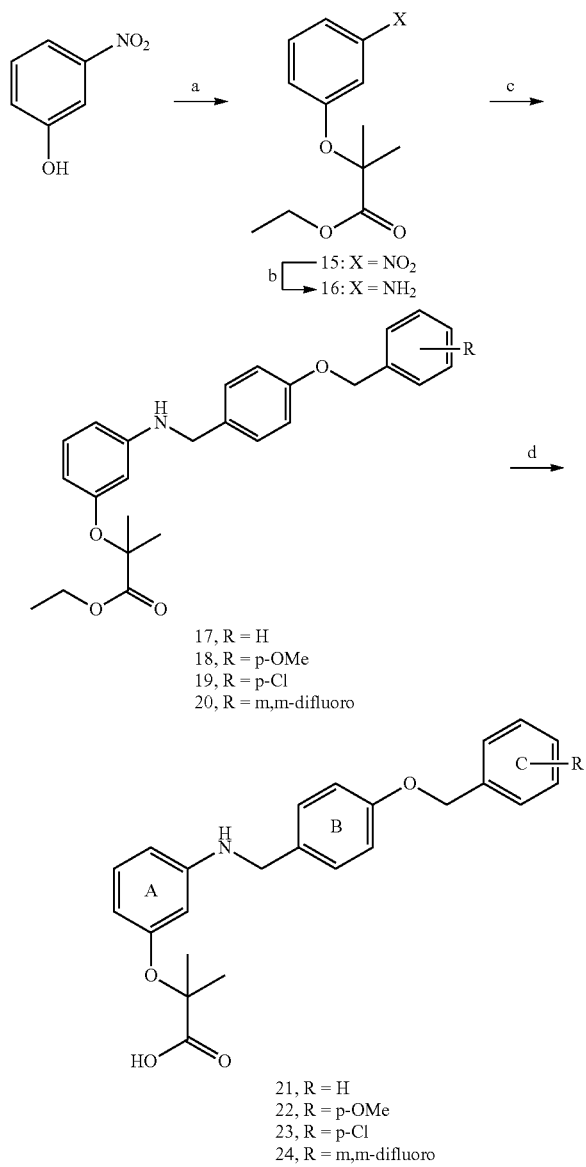

17, R = H
18, R = p-OMe
19, R = p-Cl
20, R = m,m-difluoro

21, R = H
22, R = p-OMe
23, R = p-Cl
24, R = m,m-difluoro

With the focused subset of analogs in-hand, our efforts shifted to the evaluation of these derivatives for PPARα agonism. Preliminary evaluation utilized a commercially available PPARα luciferase cell reporter assay (Indigo Biosciences). The cell-line employed is engineered to constitutively express high-levels of hPPARα. Upon interaction with an agonist, hPPARα translocates to the nucleus, binds to the PPRE, and upregulates gene transcription, including the inserted luciferase gene. Luciferase activity is detected indirectly through quantification of oxyluciferin production. Initially, 9-14 and 21-24 were evaluated at 5 µM and 50 µM to provide an idea of agonism-level at two 10-fold increments. As shown in FIG. 1, a number of compounds exhibited levels of hPPARα agonism on par with or surpassing the positive control, GW590735 (5 µM and 10 µM), at one or both of the concentrations evaluated. Direct comparison of 9/21, 10/22, 12/23, 14/24 reveals that incorporation of the fenofibrate "head-group" enhances the level of PPARα agonism at 50 µM. This data also indicates, however, that incorporation of the fenofibrate "head-group" decreases potency, as 21-24 fail to elicit appreciable activity at 5 µM, whereas the benzoic acid analogs 9-14 all exhibit significant PPARα agonism at this lower concentration. Compounds 10 and 22 were selected for more detailed evaluation, and a more expansive 10-point dose-response assessment was conducted to obtain EC50 values (Table 4): 10 (5.6 µM), and 22 (25.3 µM).

Figure 2A:
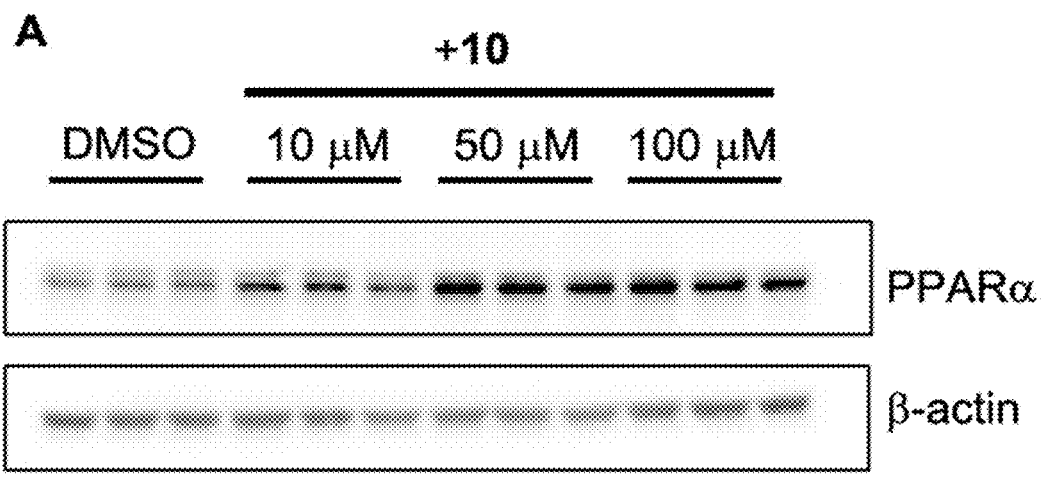
FIG. 2A shows a Western blot analysis of mouse 661W cells after 24 h treatment with 10 µM, 50 µM and 100 µM of compound 10.
Figure 2B:
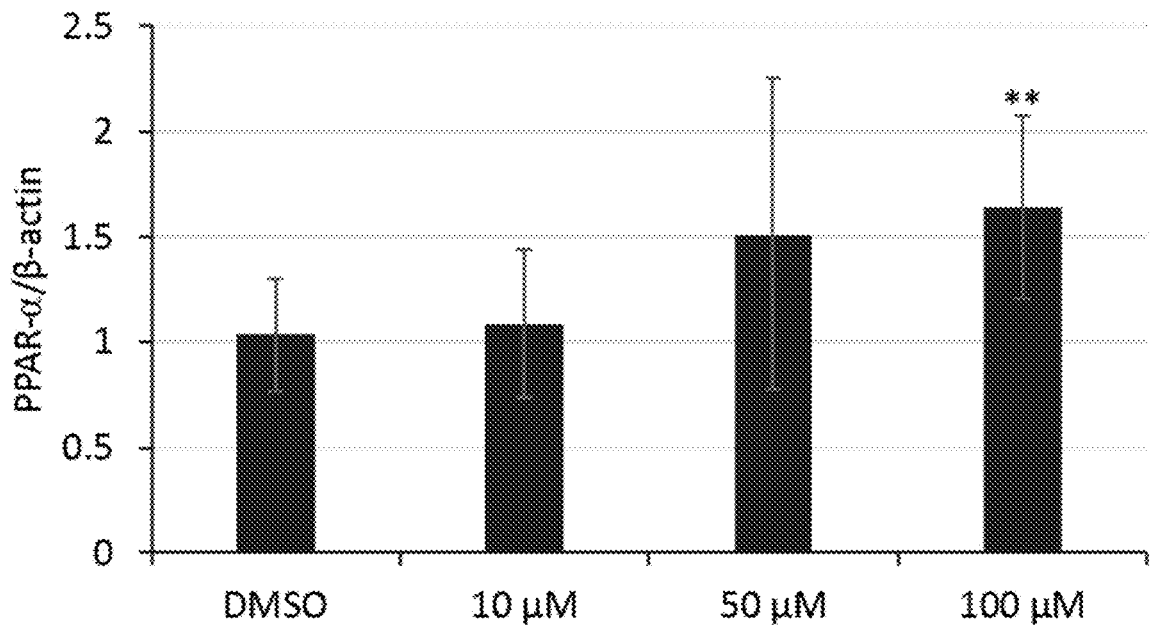
FIG. 2B shows results of a densitometry quantification of PPARα production from the Western blot analysis of FIG. 2A.
Figure 2C:
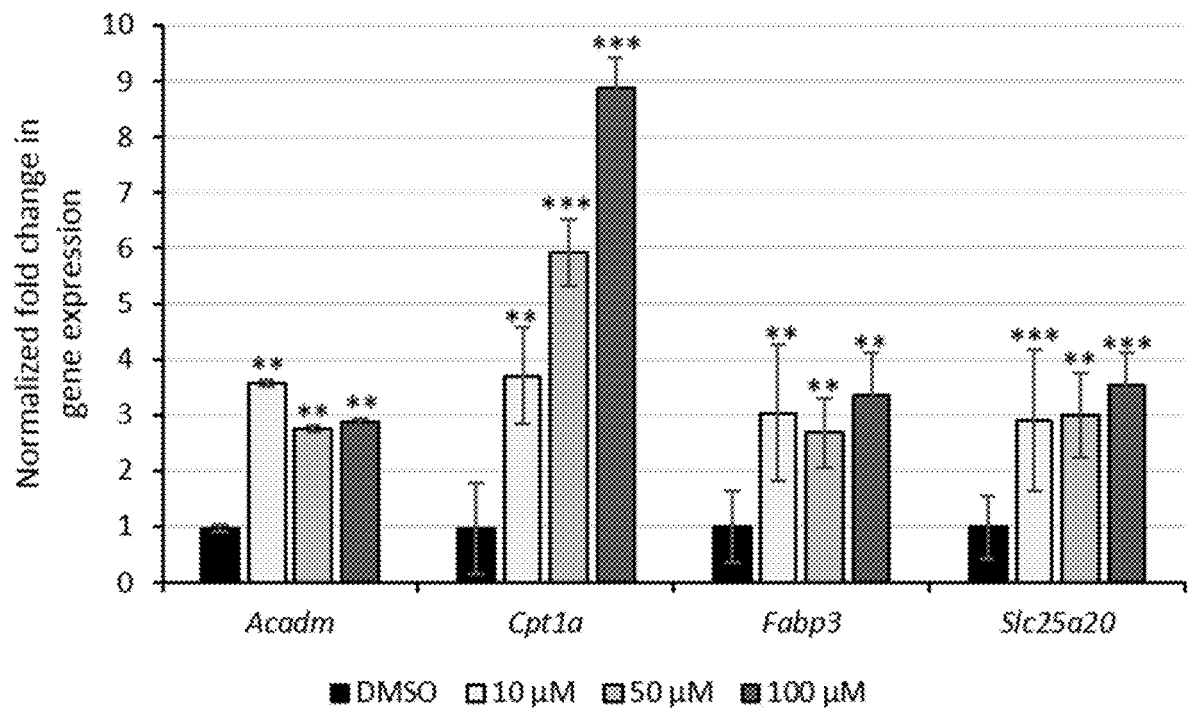
FIG. 2C shows a Real Time PCR analysis of mouse 661W cells after 24 h (n=6) treatment with compound 10.
Figure 2D:
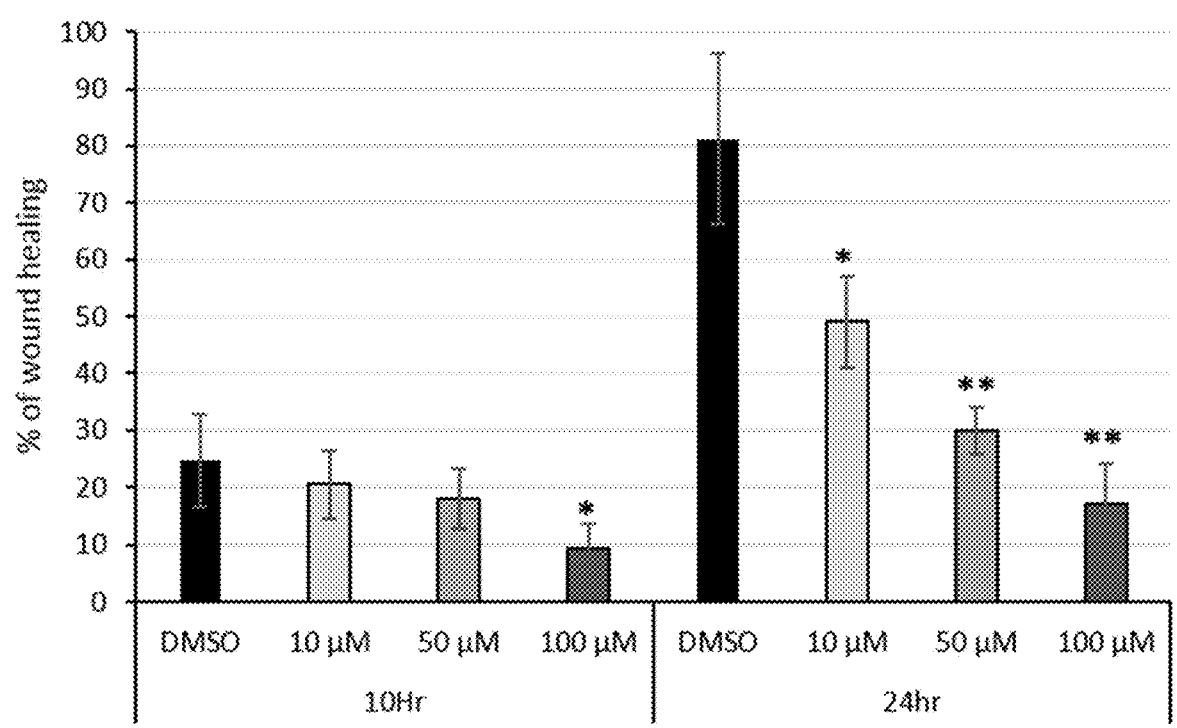
FIG. 2D shows HRCEC wound healing assay results for both 10 h and 24 h incubation time points with compound 10. Experiments in FIGS. 2A-D were performed three times in triplicate unless otherwise noted. All values shown are expressed as mean±S.D. Differences between groups were tested for statistical significance using the Student's t-test. *P<0.05. P<0.01. *P<0.001.

To further confirm that this 4-benzyloxy-benzylamino chemotype acts as a PPARα agonist, we evaluated compound 10 in various biochemical assays. As expected for a PPARα agonist, 10 induced the expression of PPARα in a dose-dependent manner (FIGS. 2A and 2B), as demonstrated by Western blot analysis using a cell line derived from C57BL/6N mouse photoreceptors (661W). Likewise, RT-PCR studies on the same cell-line confirm PPARα agonism, as treatment with 10 induces the expression of various PPARα target genes (FIG. 2C), including acyl-CoA dehydrogenase medium chain (Acadm), carnitine palmitoyltransferase 1A (Cpt1a), fatty acid binding protein 3 (Fabp3), and solute carrier family 25 member 20 (Slc25a20). Compound 10 was also evaluated in an in vitro wound healing assay utilizing human retinal capillary endothelial cells (HRCEC). PPARα agonism reduces cell migration[12] and 10, indeed, inhibits wound closure in a dose-dependent fashion (FIG. 2D).

With the evidence that 4-benzyloxy-benzylamino derivatives exhibited characteristic PPARα agonistic activity in several biological settings, the selectivity of 10 for PPARα agonism over PPARδ and PPARγ was assessed. Luciferase assays were conducted on isogenic cell-lines engineered to overexpress either PPARδ or PPARγ with expression of the requisite luciferase reporter gene dependent upon exogenous activation of each isoform. As shown in Table 4, compound 10 exhibits ≥20-fold selectivity for hPPARα over hPPARδ and hPPARγ, whereas 22 displays pan-agonism. This is interesting, as the fibrate "head-group" has been described as a critical feature for PPARα selectivity, but with this 4-benzyloxy-benzylamino chemotype it seems to be detrimental.

TABLE 4

Human PPAR agonism of select analogs.

| Compound No. | hPPARα EC₅₀(µM) | hPPARδ EC₅₀(µM) | hPPARγ EC₅₀(µM) |
|---|---|---|---|
| 10 | 5.6(1.5) | >100 | >100 |
| 22 | 25.3(1.7) | 38.6 | 18.3 |
| 26 | 5.1(1.1) | >100 | >100 |
| 28 | 2.1(1.4) | 8.9 | 5.6 |
| GW590735 | 0.012 | n.d. | n.d. |
| Rosiglitazone | n.d. | n.d. | 0.083 |
| GW0742 | n.d | 0.002 | n.d. |
| Y-0452 | 52.4 (0.3) | n.d. | n.d. |

Data are represented as the EC₅₀ (µM) for the agonism of the corresponding luciferase reporter cell-lines (Indigo Biosciences). Dosing was done in triplicate as a single experiment.
n.d. = not determined.
Values in parentheses indicate the ratio of agonism compared to GW590735.

Figure 3:
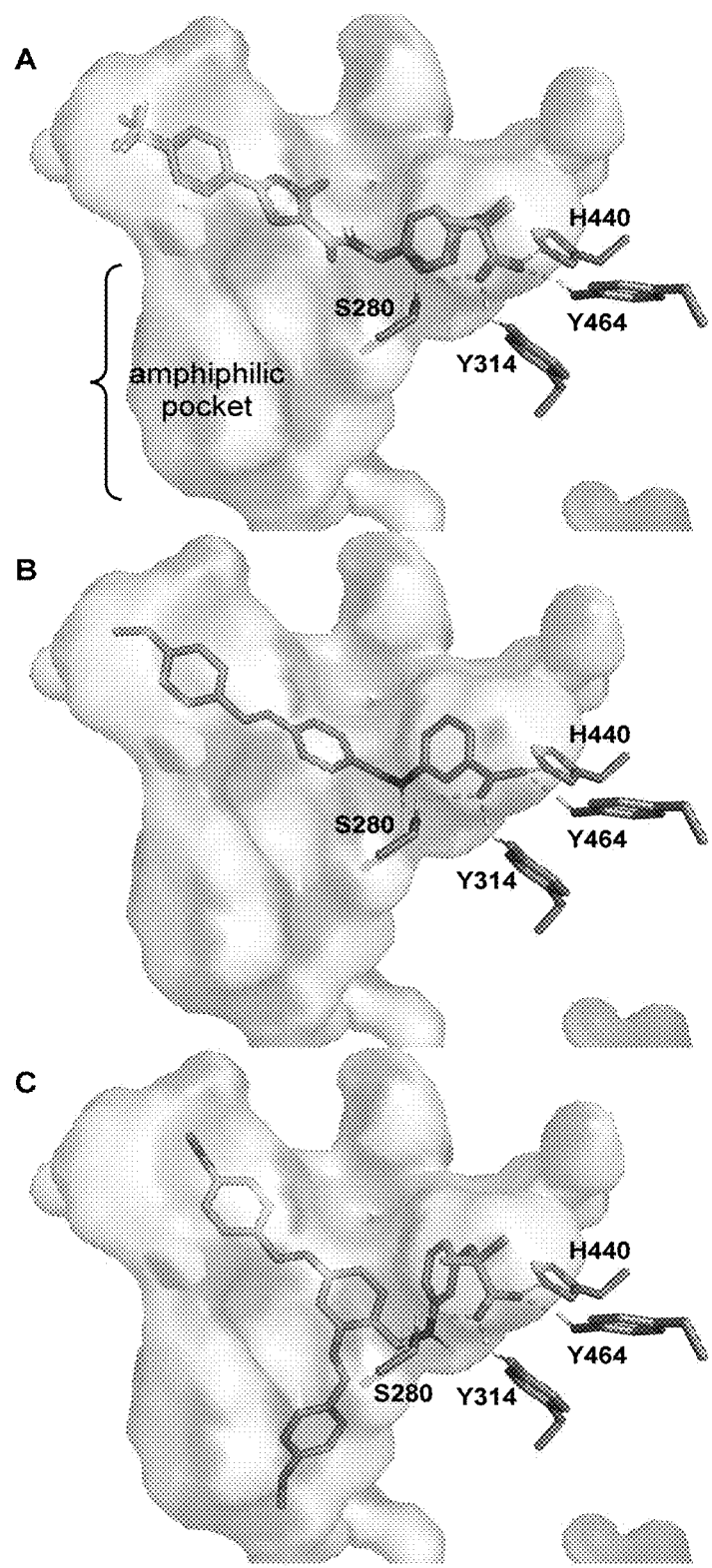
FIG. 3 shows (A) the GW590735●hPPARα co-crystal structure. (B) the predicted binding pose of 10 hPPARα, and (C) the predicted binding pose of compound 28 on hPPARα. Binding pocket cavity depicted by surface representation, PDB: 2P54.

To better visualize the 4-benzyloxy-benzylamino derivatives in the hPPARα binding pocket, we utilized PDB 2P54, the GW590735●hPPARα co-crystal structure, for docking assessment. GW590735 is a selective PPARα agonist that exhibits ≥500-fold selectivity for PPARα over PPARγ and PPARδ. Without wishing to be bound by theory, as shown in FIGS. 3A and 3B, compound 10 is predicted to bind in an orientation similar to GW590735. Interestingly, however, 10 lacks the gem-dimethyl "head-group" and amide linker domain, both of which previously have been postulated to be critical determinants in GW590735 selectivity and major enhancers of potency. The acid, however, for 10 is predicted to make four hydrogen bonds with Ser280, Tyr314, His440, and Tyr464, consistent with the idea that deconstruction of the Y-0452 quinoline core and transposition of the carboxylic acid would provide a significant improvement in PPARα agonism. We were interested if this 4-benzyloxybenzylamino chemotype could be expanded to take advantage of an apparent amphiphilic pocket that lies below GW590735 (FIG. 3A) and is comprised of Met330, Tyr334, Glu282, Thr279, Met320, Val324, Leu321, Ile317, and Met220. We postulated that functionalization of the B-ring meta to the ether linkage (Schemes 5 and 6) on 10 would provide an optimal trajectory for accessing this amphiphilic pocket. To the best of our knowledge, few PPARα agonists exploit this pocket and little SAR exists regarding the effect of occupying this domain on the level of agonism and/or isoform selectivity.

To investigate the possible impact of occupying the amphiphilic pocket, we synthesized two additional derivatives, 26 and 28 (Scheme 6). Briefly, commercially available 2,4-dihydroxybenzaldehyde was treated with 4-methoxybenzaldehyde in the presence of potassium carbonate in acetone to produce the di-p-methoxybenzyl (PMB) functionalized resorcinol 25. This intermediate was coupled to either 3-aminobenzoic acid or 16 followed by reduction of the resulting imine to provide analog 26 and the methyl ester 27, respectively. Following saponification of 27, the desired derivative 28 was obtained in 75% yield. Incorporation of the 4-methoxybenzyl motif as the "third-arm" was rather arbitrary at this point and was selected on belief that it 1) would be compatible with the predicted binding environment and 2) could be easily synthesized through dialkylation of an aldehyde already in our chemical inventory.

Scheme 6. Synthesis of derivatives 26 and 27. Reagents and conditions: (a) 4-methoxybenzyl bromide, $K_2CO_3$, Acetone; (b) 3-aminobenzoic acid or 16 toluene, 155° C., 2 h; sodium triacetoxyborohydride, AcOH, THF, 0° C. to 25° C., 12 h; (c) LiOH·$H_2O$, THF/MeOH/$H_2O$, 12 h.

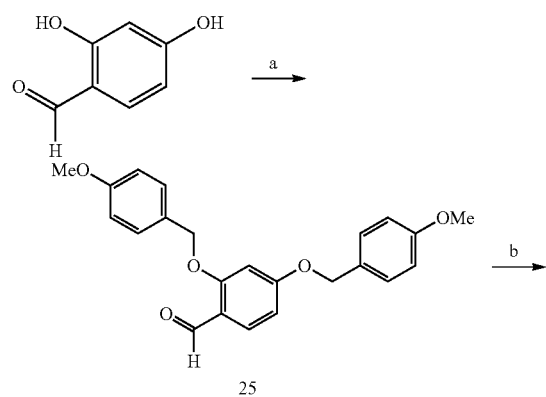

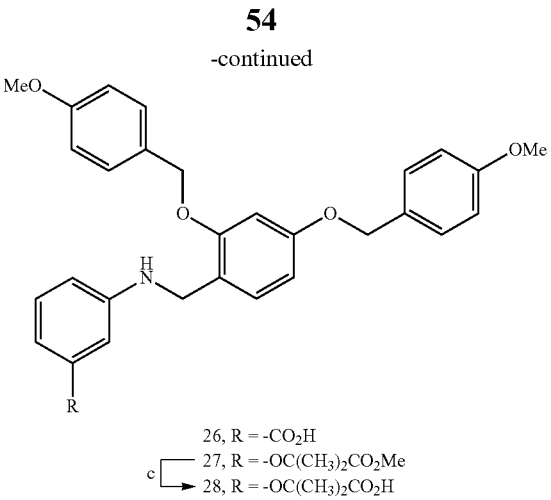

Derivatives 26 and 28 were evaluated for hPPARα agonistic activity and selectivity in the luciferase cell-lines. Analysis of the data suggests that regarding the benzoic acid derivatives (compare 10 and 26), the additional 4-methoxybenzyl substituent does not affect potency and maintains the selectivity, at least within the range of doses evaluated. For derivatives containing the fibrate "head-group" (compare 22 and 28), however, the addition of the third substituent on the B-ring resulted in a 10-fold improvement in potency, but the pan-agonist profile was maintained. Both 26 and 28 were docked using our previously generated model and as can be seen in FIG. 3C the additional 4-methoxybenzyl group is, indeed, predicted to extend into the amphiphilic pocket.

Various non-limiting embodiments of the compounds of the present disclosure and their cellular luciferase activities are shown in Tables 5-8. Chemical structure IIa (Tables 5 and 6) is a version of chemical structure II in which k=0. Chemical structure IIb (Tables 7 and 8) is version of chemical structure IIa wherein the $R^1$ group is in the para position on Ring A.

Structure IIa

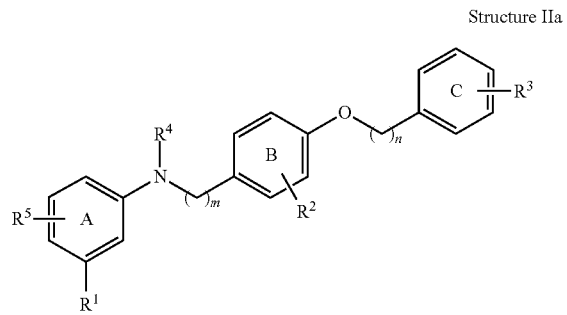

TABLE 5

Representative Examples of Compounds having Chemical Structure IIa

| R[1] | R[4] | m | n | R[3] | R[2] | R[5] | Compound No. (Alternate no.) |
|---|---|---|---|---|---|---|---|
| COOH | H | 1 | 1 | 4-OCH$_3$ | H | H | 91, (10) |
| COOH | H | 1 | 1 | 4-OCH$_3$ | 3-OPMB[1] | H | 92, (26) |
| B(OH)$_2$ | H | 1 | 1 | 4-OCH$_3$ | H | H | 110 |
| OC(CH$_3$)$_2$COOH | H | 1 | 1 | 4-OCH$_3$ | H | H | 114, (22) |
| OC(CH$_3$)$_2$COOH | H | 1 | 1 | 4-OCH$_3$ | 3-OPMB[1] | H | 115, (28) |
| OC(CH$_3$)$_2$COOH | H | 1 | 1 | H | H | H | 116, (21) |
| COOH | H | 1 | 1 | H | H | H | 117, (9) |
| COOH | H | 1 | 1 | 2,4-dichloro | H | H | 118, (13) |
| COOH | H | 1 | 1 | 3,5-difluoro | H | H | 119, (14) |
| COOH | H | 1 | 1 | 4-NO$_2$ | H | H | 120, (11) |
| OC(CH$_3$)$_2$COOH | H | 1 | 1 | 3,5-difluoro | H | H | 121, (24) |
| COOH | H | 1 | 1 | 4-Cl | H | H | 122, (12) |
| OC(CH$_3$)$_2$COOH | H | 1 | 1 | 4-Cl | H | H | 123, (23) |
| COOH | H | 1 | 1 | 4-F | H | H | 125 |
| COOH | H | 1 | 1 | 4-CF$_3$ | H | H | 126 |
| OC(CH$_3$)$_2$COOH | H | 1 | 1 | 4-F | H | H | 127 |
| OC(CH$_3$)$_2$COOH | H | 1 | 1 | 4-CF$_3$ | H | H | 128 |
| OCH$_2$COOH | H | 1 | 1 | 4-CF$_3$ | H | H | 129 |
| OCH$_2$COOH | H | 1 | 1 | 4-OCH$_3$ | H | H | 130 |
| COOH | H | 2 | 2 | H | H | H | 133 |
| C(O)NHOH | H | 1 | 1 | 4-OCH$_3$ | H | H | 134 |
| NHSO$_2$CH$_3$ | H | 1 | 1 | 4-F | H | H | 145 |
| C(O)NHOH | H | 1 | 1 | 4-F | H | H | 146 |
| SO$_2$NH$_2$ | H | 1 | 1 | 4-F | H | H | 147 |
| tetrazole | H | 1 | 1 | 4-F | H | H | 148 |
| COOH | CH$_3$ | 1 | 1 | 4-F | H | H | 151 |
| OC(CH$_3$)$_2$COOH | CH$_3$ | 1 | 1 | 4-F | H | H | 153 |
| B(OH)$_2$ | H | 1 | 1 | 4-F | H | H | 154 |
| COOH | H | 1 | 1 | 4-F | H | 4-F | 158 |
| COOH | H | 1 | 1 | 4-OCH$_3$ | H | 4-F | 159 |
| COOH | H | 1 | 1 | 4-F | H | 5-Cl | 168 |
| COOH | H | 1 | 1 | 4-F | H | 6-CH$_3$ | 174 |
| COOH | H | 1 | 1 | 4-F | H | 5-Br | 184 |
| COOH | H | 1 | 1 | 4-F | H | 5-F | 185 |
| COOH | H | 2 | 2 | 4-OCH$_3$ | H | H | 187 |
| SC(CH$_3$)$_2$COOH | H | 1 | 1 | 4-F | H | H | 188 |
| COOH | H | 1 | 1 | 4-I | H | H | 189 |
| COOH | H | 1 | 1 | 4-F | 2-CH$_3$ | H | 190 |
| COOH | H | 1 | 1 | 4-CN | H | H | 191 |
| COOH | H | 1 | 1 | 4-Br | H | H | 192 |
| COOH | H | 1 | 1 | 3-F | H | H | 193 |
| COOH | H | 1 | 1 | 2,4-difluoro | H | H | 194 |
| COOH | H | 1 | 1 | 2-F | H | H | 195 |
| COOH | H | 1 | 1 | 2,4-difluoro | 2-CH$_3$ | H | 196 |
| COOH | H | 1 | 1 | 3,4-difluoro | 2-CH$_3$ | H | 197 |
| COOH | H | 1 | 1 | 3,5-difluoro | 2-CH$_3$ | H | 198 |
| COOH | CH$_3$ | 1 | 1 | 4-F | 2-CH$_3$ | H | 199 |
| COOH | H | 1 | 1 | 4-F | 3-CH$_3$ | H | 201 |
| COOH | H | 1 | 1 | 4-F | 2-OPFB[2] | H | 202 |
| COOH | H | 1 | 1 | 4-F | 2-F | H | 204 |
| COOH | H | 1 | 1 | 4-F | 2-F | H | 206 |
| OC(CH$_3$)$_2$COOH | H | 1 | 1 | 4-F | 2-CH$_3$ | H | 208 |

[1]OPMB represents-O-para-methoxybenzyl;
[2]OPFB represents-O-para-fluorobenzyl.

TABLE 6

Cellular Luciferase Activity

| Compound No. | Fold[a] (5 µM) | Fold[a] (50 µM) | α EC$_{50}$[b] | γ EC$_{50}$[b] | δ EC$_{50}$[b] |
|---|---|---|---|---|---|
| 91, (10) | 11 | 36 | 5.6 | >100 | >100 |
| 92, (26) | 8 | 21 | 5.1 | >100 | >100 |
| 110 | 1 | 1 | | | |
| 114, (22) | 1 | 59 | 25.3 | 38.6 | 18.3 |
| 115, (28) | 1 | 41 | 2.1 | 8.9 | 5.6 |
| 116, (21) | 1 | 46 | | | |
| 117, (9) | 18 | 35 | | | |
| 118, (13) | 1 | 37 | | | |
| 119, (14) | 9 | 35 | | | |
| 120, (11) | 16 | 35 | | | |
| 121, (24) | 16 | 42 | | | |
| 122, (12) | 17 | 36 | | | |
| 123, (23) | 2 | 55 | | | |
| 125 | 82 | 97 | 0.8 | >100 | >100 |
| 126 | 81 | 100 | 0.8 | | |
| 127 | 11 | 150 | | | |
| 128 | 19 | 106 | | | |
| 129 | 2 | 112 | | | |
| 130 | 2 | 43 | 29.2 | | |
| 133 | 1 | 0 | | | |

TABLE 6-continued

Cellular Luciferase Activity

| Compound No. | Fold[a] (5 μM) | Fold[a] (50 μM) | α $EC_{50}$[b] | γ $EC_{50}$[b] | δ $EC_{50}$[b] |
|---|---|---|---|---|---|
| 134 | 3 | 9 | | | |
| 145 | 3 | 5 | | | |
| 146 | 34 | 53 | | | |
| 147 | 3 | 3 | | | |
| 148 | 73 | 85 | 5.7 | | |
| 151 | 102 | 109 | 1.0 | | |
| 153 | 94 | 120 | 1.7 | | |
| 154 | 3 | 2 | | | |
| 158 | 100 | 140 | 1.3 | | |
| 159 | 45 | 121 | | | |
| 168 | 18 | 93 | | | |
| 174 | 2 | 25 | | | |
| 184 | 59 | 69 | 0.9 | | |
| 185 | 61 | 66 | 0.7 | >100 | >100 |
| 187 | 1 | 0 | | | |
| 188 | 10 | 45 | | | |
| 189 | 39 | 37 | 1.2 | | |
| 190 | 69 | 44 | 0.03 | >100 | >100 |
| 191 | 42 | 61 | | | |
| 192 | 53 | 58 | 0.8 | | |
| 193 | 73 | 56 | 1.1 | | |
| 194 | 51 | 49 | 0.4 | >100 | >100 |
| 195 | 34 | 45 | | | |
| 196 | 74 | 72 | | | |
| 197 | 69 | 70 | | | |
| 198 | 88 | 84 | | | |
| 199 | 102 | 131 | | | |
| 201 | 56 | 81 | | | |
| 202 | 74 | 63 | | | |
| 204 | 92 | 102 | | | |
| 206 | 97 | 64 | | | |
| 208 | 78 | 66 | | | |

[a]Fold = fold increase in luciferase compared to DMSO negative control. These values cannot necessarily be used to compare two compounds, as runs may not have occurred under the same conditions.
[b]$EC_{50}$ = compound concentration (μM) that produces 50% maximal activity.

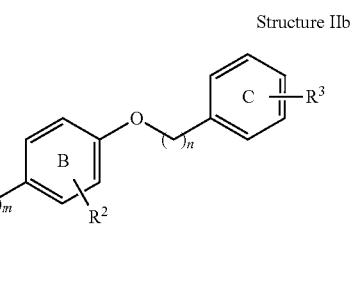

Structure IIb

TABLE 7

Representative Examples of Compounds having Chemical Structure IIb

| $R^1$ | $R^4$ | m | n | $R^3$ | $R^2$ | $R^5$ | Compound No. |
|---|---|---|---|---|---|---|---|
| COOH | H | 1 | 1 | 4-$CF_3$ | H | H | 155 |
| COOH | H | 1 | 1 | 4-$OCH_3$ | H | H | 162 |
| OC($CH_3$)$_2$COOH | H | 1 | 1 | 4-F | H | H | 182 |
| COOH | H | 1 | 1 | 4-F | H | H | 183 |

TABLE 8

Cellular Luciferase Activity

| Compound No. | Fold[a] (5 μM) | Fold[a] (50 μM) |
|---|---|---|
| 155 | 4 | 8 |
| 162 | 4 | 29 |
| 182 | 40 | 74 |
| 183 | 4 | 14 |

[a]Fold = fold increase in luciferase compared to DMSO negative control. These values cannot necessarily be used to compare two compounds, as runs may not have occurred under the same conditions.

Figure 4:
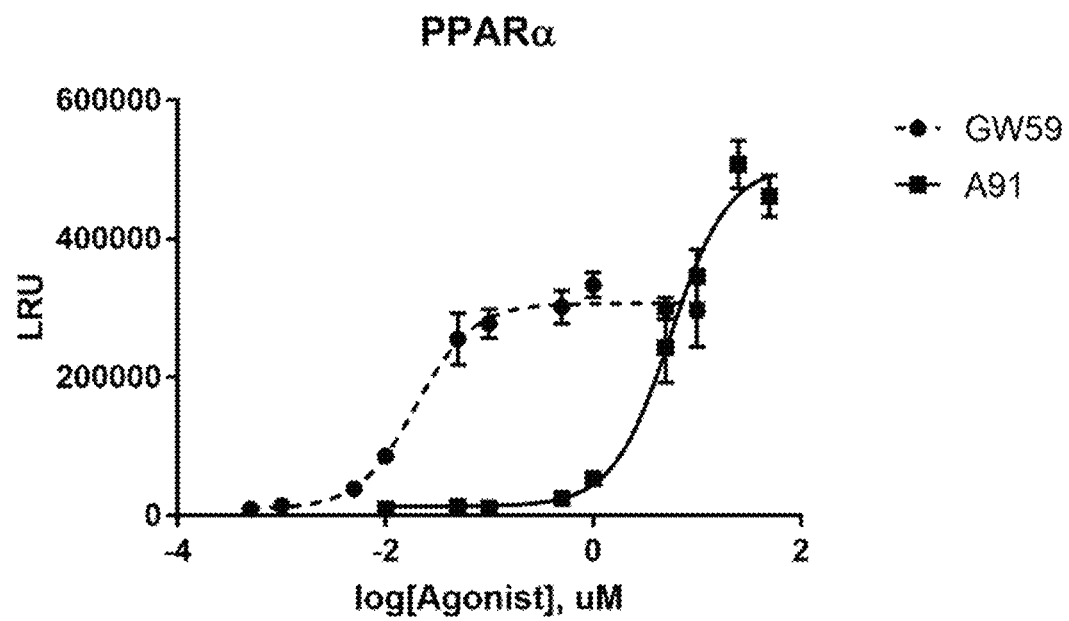
FIG. 4 shows dose-dependent agonism of PPARα by A91 as demonstrated by luciferase quantification (luminescence) in a cell-based luciferase reporter assay. GW 59=GW590735 employed as a positive control. (A91=ASD91=10).
Figure 5:
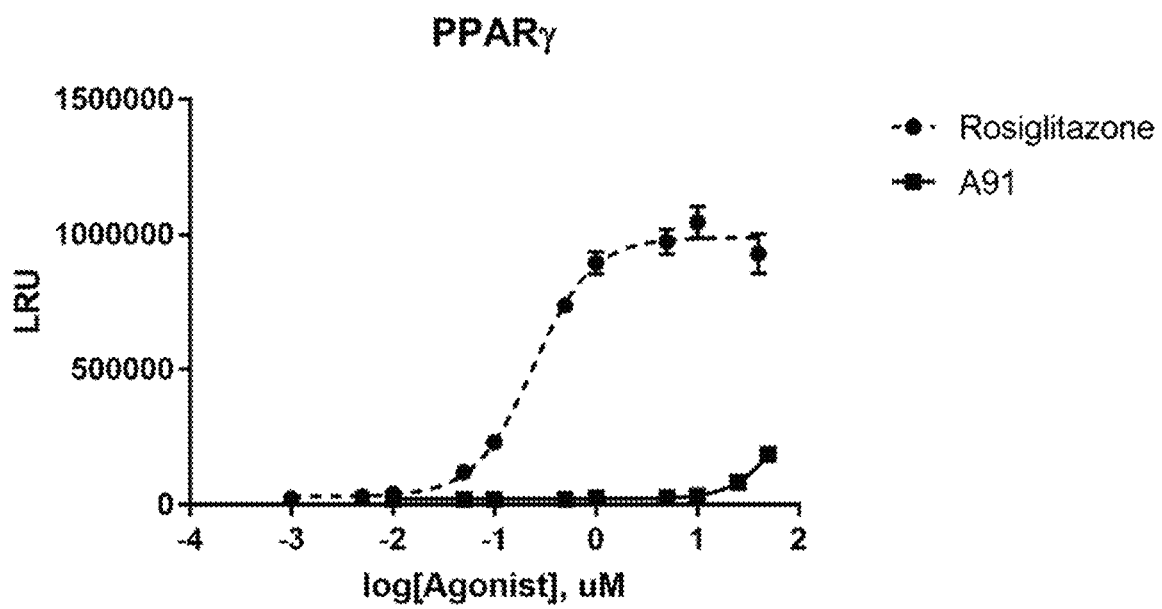
FIG. 5 shows dose-dependent agonism of PPARγ by A91 as demonstrated by luciferase quantification (luminescence) in a cell-based luciferase reporter assay. Rosiglitazone employed as a positive control. (A91=ASD91=10).
Figure 6:
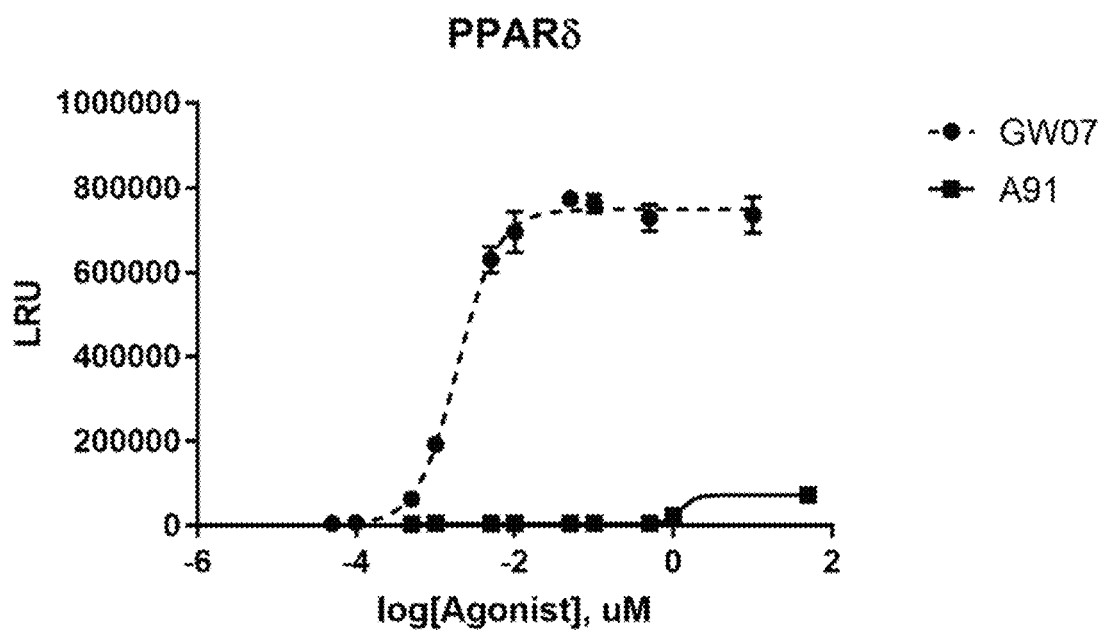
FIG. 6 shows dose-dependent agonism of PPARδ by A91 as demonstrated by luciferase quantification (luminescence) in a cell-based luciferase reporter assay. GW 07=GW0742 employed as a positive control. (A91=ASD91=10).
Figure 7:
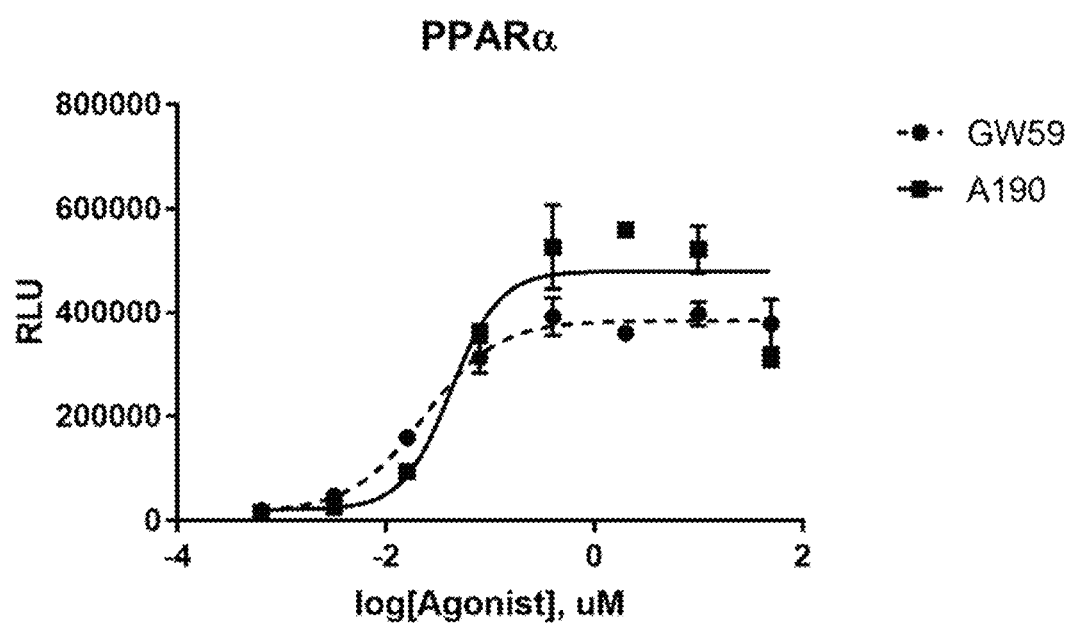
FIG. 7 shows dose-dependent agonism of PPARα by A190 as demonstrated by luciferase quantification (luminescence) in a cell-based luciferase reporter assay. GW 59=GW590735 employed as a positive control. (A190=190=ASD190).
Figure 8:
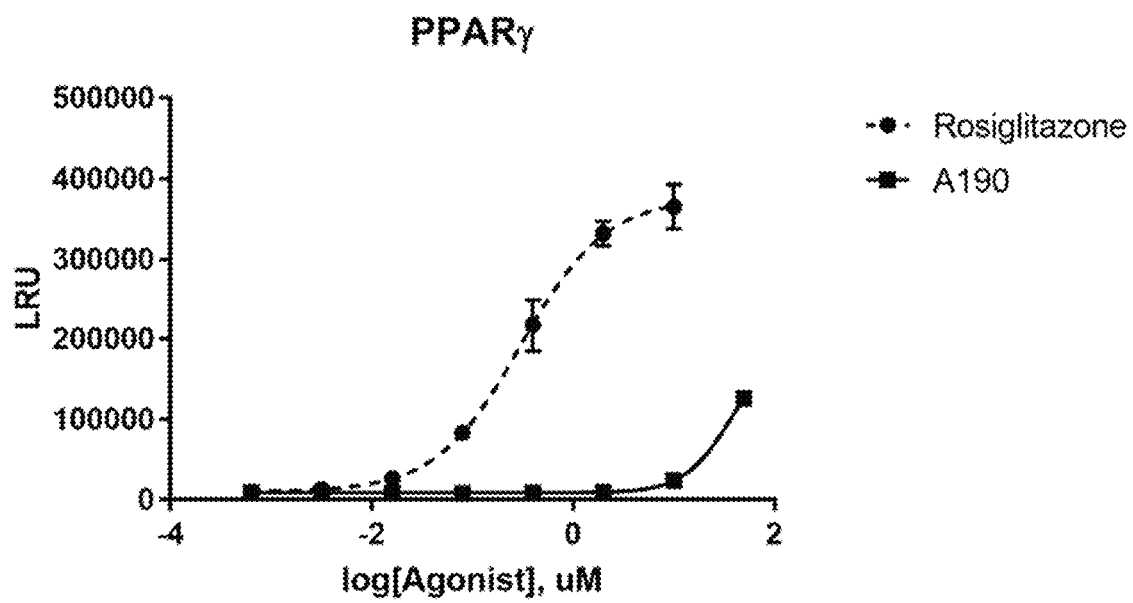
FIG. 8 shows dose-dependent agonism of PPARγ by A190 as demonstrated by luciferase quantification (luminescence) in a cell-based luciferase reporter assay. Rosiglitazone employed as a positive control. (A190=190=ASD190).
Figure 9:
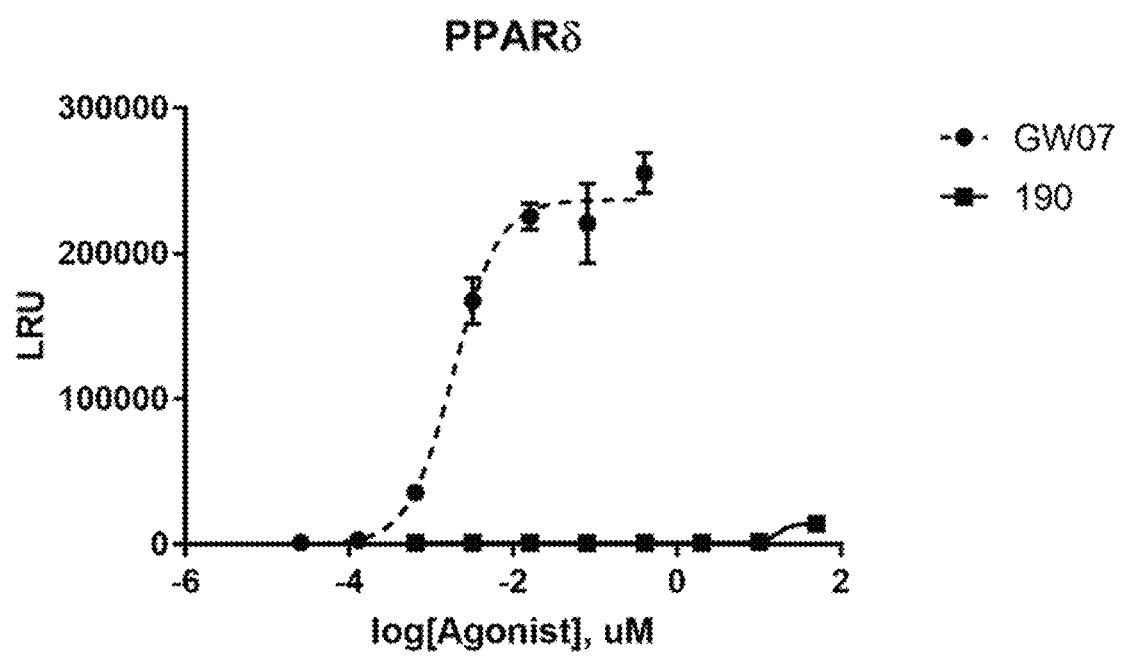
FIG. 9 shows dose-dependent agonism of PPARδ by A190 as demonstrated by luciferase quantification (luminescence) in a cell-based luciferase reporter assay. GW 07=GW0742 employed as a positive control. (A190=190=ASD190).

The data in Tables 5-8 demonstrate that this chemotype is active in a whole-cell setting and engages the desired target, PPARα. Additionally, the results demonstrate definitive structure-activity relationships, a tunable level of agonism, and the selectivity profile of this chemotype for PPARα over the other isoforms. The results shown in FIGS. 4-6 demonstrate that compound 91 (10) exhibits dose-dependent activity in a cell-based activity and exhibits >20-fold selectivity over other isoforms. The results shown in FIGS. 7-9 demonstrate that compound 190 exhibits dose-dependent activity in a cell-based activity and exhibits >2000-fold selectivity over other isoforms.

This demonstrates that potency of this chemotype can be improved while enhancing or maintaining selectivity.

Figure 10A:
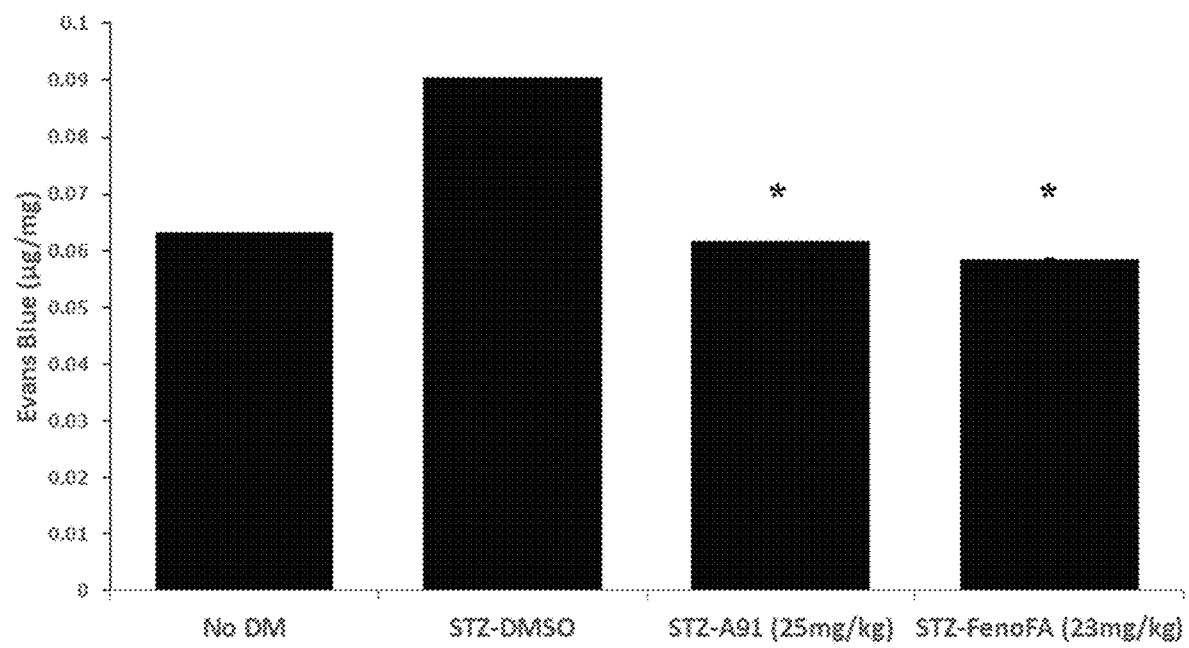
FIG. 10A shows results of the in vivo efficacy of Compound ASD91 (10) on retinal permeability in comparison to fenofibric acid (FenoFA). 7-8 week-old male Brown Norway rats were injected with streptozotocin (STZ, 55 mg/kg). Two weeks after STZ injections, daily treatment (i.p. injection) with ASD091 or FenoFA commenced and lasted for 26-28 days. ≠P<0.05 (vs. FenoFA), *P<0.05 (vs. STZ-DMSO).
Figure 10B:
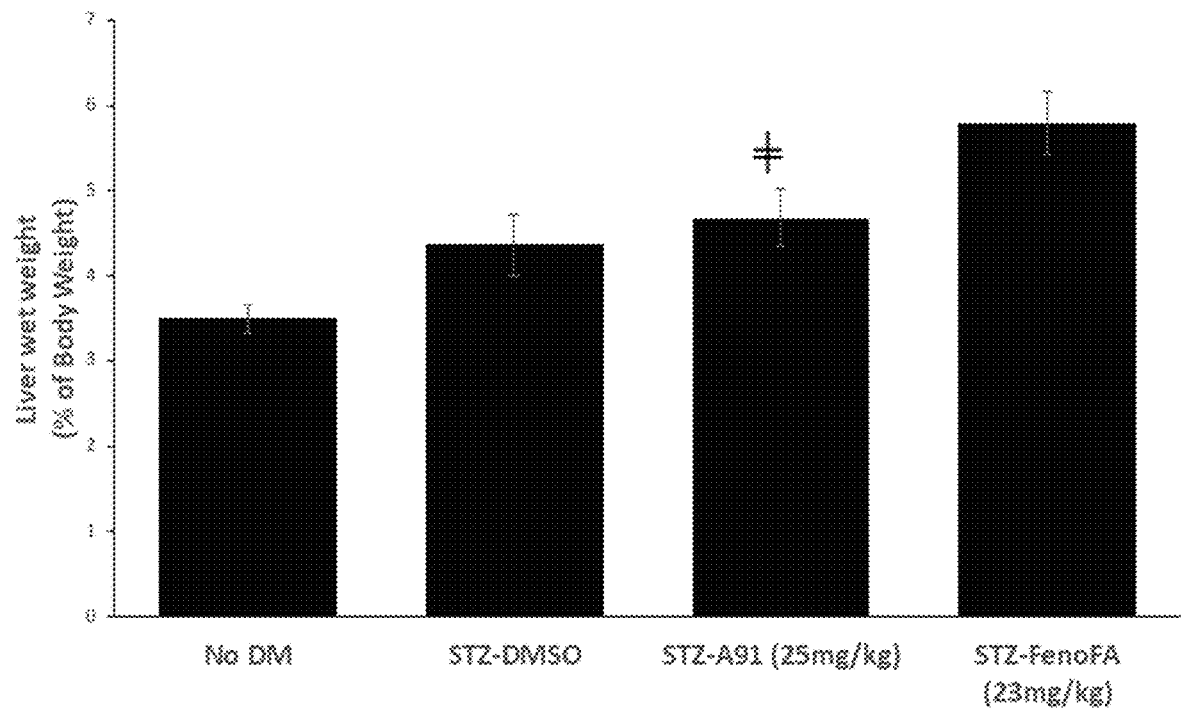
FIG. 10B shows results of the in vivo efficacy of Compound ASD91(10) on liver phenotype in comparison to fenofibric acid (FenoFA). 7-8 week-old male Brown Norway rats were injected with streptozotocin (STZ, 55 mg/kg). Two weeks after STZ injections, daily treatment (i.p. injection) with ASD091 or FenoFA commenced and lasted for 26-28 days. ≠P<0.05 (vs. FenoFA), *P<0.05 (vs. STZ-DMSO).

The data in FIGS. 10A and 10B show that pharmacological activation of PPARα in humans has clinical benefits on reducing the prevalence of diabetic retinopathy, as reported in FIELD and ACCORD studies. We demonstrate in FIGS. 10A and 10B that compound 91 exhibits in vivo efficacy in a well-established STZ-rat model of diabetic retinopathy (DR). As shown in FIGS. 10A and 10B, compound 91 reduces retinal vascular leakage in diabetic rats—a major culprit behind diabetic macular edema and consequential vision loss. Of interesting note, compound 91 seems to lack signs of hepatomegaly, a common side-effect of fenofibrate that may impose dose-limiting toxicity. These initial results provide proof-of-concept that compound 91 (1) demonstrates in vivo efficacy in a relevant DR model following systemic administration, (2) crosses blood-ocular barrier and reaches the retina, (3) is bioavailable, (4) survives first-pass metabolism and clearance mechanisms well enough to maintain efficacy, and (5) demonstrates a relatively safe profile (no observable toxicity) after daily injection for one-month.

In at least certain ermbodiments of the present disclosure, the compounds have agonistic activity which is highly selective for PPARα as compared to the isoforms PPARγ, and PPARδ. For example, the PPARα agonistic activity may be 1000-fold, or 2000-fold, or 2500-fold, or greater than the compound's agonistic activity for either PPARγ or PPARδ. Compound 190 (A190) for example has been found to be particularly potent, having an $EC_{50}$ of 37 nm and having a >2700-fold selectivity for PPARα versus the isoforms PPARγ, and PPARδ (calculated as $EC_{50}$ (PPARγ)/$EC_{50}$ (PPARα) or $EC_{50}$ (PPARδ)/$EC_{50}$ (PPARα).

Table 9 shows several compounds of the disclosure (particular embodiments of chemical structure II) and activities, including PPARα activities, thereof.

TABLE 9

Compounds and Activities

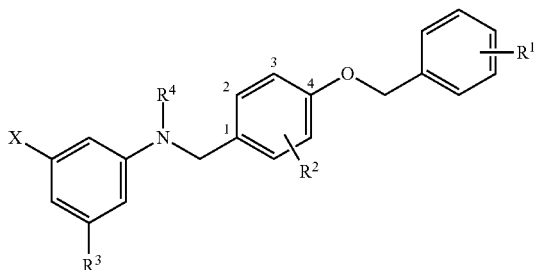

| Compound Identifier | X | $R^1$ | $R^2$ | $R^3$ | $R^4$ | ratio (5/50) | fold-signal | $EC_{50}$ hPPARα(μM) |
|---|---|---|---|---|---|---|---|---|
| 20' | COOH | 4-Cl | 3-Me | H | H | 1.2 | 1.2 | 0.029 + 0.001 |
| 21' | COOH | 4-Br | 3-Me | H | H | 1.2 | 1.3 | 0.031 ± 0.008 |
| 22' | COOH | 4-I | 3-Me | H | H | 1.8 | 1.5 | 0.027 + 0.003 |
| 23' | COOH | 2,4-diF | 3-Me | H | H | 1.2 | 1.4 | 0.056 ± 0.007 |
| 24' | COOH | 3,4-diF | 3-Me | H | H | 1.4 | 1.6 | 0.018 ± 0.001 |
| 25' | COOH | 3,5-diF | 3-Me | H | H | 1.1 | 1.6 | |
| 26' | COOH | 4-F | 3-F | H | H | 0.7 | 1.7 | |
| 27' | COOH | 4-F | 3-Cl | H | H | 1.1 | 1.5 | |
| 28' | COOH | 4-OPFB | 3-OPFB | H | H | 1.0 | 1.4 | 0.81 ± 0.17 |
| 29' | COOH | 4-OPFB | 3-OPFB | H | H | 0.9 | 1.2 | 0.93 ± 0.02 |
| 30' | COOH | 4-F | 3-Me | H | Me | 0.8 | 2.1 | 0.067 ± 0.01 |
| 31' | COOH | 4-F | 3-Me | F | H | 0.9 | 1.5 | 0.040 ± 0.001 |
| 32' | COOH | 4-F | 3-Cl | F | H | 1.1 | 1.8 | 0.052 ± 0.011 |
| 33' | OC(CH$_3$)$_2$COOH | 4-F | 3-Me | H | H | 1.0 | 1.6 | 0.74 ± 0.04 |
| 4a (91) | COOH | 3-OMe | H | H | H | 0.5 | 1.4 | 4.43 ± 0.01 |
| 4b | COOH | 4-F | H | H | H | 0.8 | 1.3 | 0.77 ± 0.03 |
| 190 (A190) | COOH | 4-F | 3-Me | H | H | | | 0.037 ± 0.001 |
| GW590735 | | | | | | 1.0 | 1.0 | 0.015 ± 0.002 |

Ratio (5/50): Ratio of relative light unit (RLU) signal at 5 and 50 μM compound concentrations.
Fold-signal: Ratio of signal maximal signal strength observed for the compound of interest to that obtained with compound GW590735.
$EC_{50}$hPPARα(μM): mean ± SEM of at least two separate experiments performed in triplicate.
OPFB = O-para-fluorobenzyl.
Numbering shown is based on the name of the resulting products.
Blank cells indicate compound was not selected for testing in the corresponding assay.

In conclusion, in at least certain embodiments, the present disclosure is directed to a compound comprising chemical structure III:

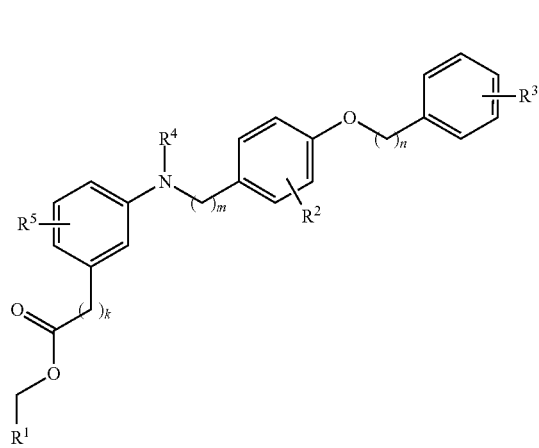

III and salts and isomers thereof, wherein (1) k is 0, 1, 2, 3, 4, 5, 6, 7, 8, 9, or 10 carbon atoms, (2) m is 0, 1, 2, 3, 4, or 5 carbon atoms, (3) n is 0, 1, 2, 3, 4, or 5 carbon atoms, (4) $R^1$ is selected from phosphate and phosphonate, (5) $R^2$ is selected from CH$_3$, hydrogen (H), chlorine (Cl), fluorine (F), bromine (Br), iodine (I), nitro (NO$_2$), CH$_2$CH$_3$, branched or unbranched alkyl chains with 3-10 carbon atoms, OCH$_3$, OCH$_2$CH$_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^2$ comprises one, two, three, or four of said $R^2$ substituents substituted in any combination of said $R^2$ substituents and arranged in any pattern in the ring including ortho, meta, mono, di, tri, and tetrasubstituted, (6) $R^3$ is selected from F, H, Cl, Br, I, NO$_2$, CH$_3$, CH$_2$CH$_3$, branched or unbranched alkyl chains with 3-10 carbon atoms, OCH$_3$, OCH$_2$CH$_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^3$ comprises one, two, three, four, or five of said $R^3$ substituents substituted in any combination of said $R^3$ substituents and arranged in any pattern in the ring including ortho, meta, para, mono, di, tri, tetra, and pentasubstituted, (7) $R^4$ is selected from H, alkyl, and acyl, and (8) $R^5$ is selected from H, Cl, F, Br, I, NO$_2$, CH$_3$, CH$_2$CH$_3$, branched or unbranched alkyl chains with 3-10 carbon atoms, OCH$_3$, OCH$_2$CH$_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^5$ comprises one, two, three, or four of said $R^5$ substituents and arranged in any pattern in the ring including ortho, meta, para, mono, di, tri, and tetrasubstituted, wherein the compound has PPARα agonistic activity. $R^1$ may be a phosphate having the chemical structure:

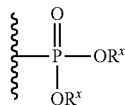

wherein each $R^x$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine. $R^1$ imay be a phosphonate having the chemical structure:

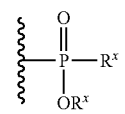

wherein each $R^x$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine.

The compound's PPARα agonistic activity may be at least 1,000-fold greater than the compound's PPARγ agonistic activity or PPARδ agonistic activity. One or more of the compounds may be disposed in a pharmaceutically-acceptable carrier, vehicle, or diluent to form a composition. The composition may be formulated to provide a delayed release, controlled release, extended release, and/or sustained release of the one or more compounds. The compound or composition may be a component of a kit. The kit may include instructions for use thereof in a treatment of a disorder or condition in a subject. The disorder or condition for which the kit may be used in treatment may be an ocular disorder or condition such as retinal inflammation, retinal neovascularization, retinal vascular leakage, retinopathy of prematurity (ROP), diabetic retinopathy (DR), an age-related macular degeneration (AMD), macular edema, diabetic macular edema (DME), keratitis, endophthalmitis, blepharitis, conjunctivitis, scleritis, herpetic inflammation, uveitis, vasculitis, arteritis, orbital inflammations, optic neuritis, sympathetic ophthalmia, retinitis, glaucoma, proliferative vitreoretinopathy, corneal edema, uveal edema, or retinal edema.

In at least certain embodiments, the present disclosure is directed to a method of increasing PPARα activity in a retinal cell by administering to the retinal cell a PPARα activity-enhancing amount of the compound or composition described above. In at least certain embodiments, the present disclosure is directed to a method of treating a disorder or condition in a subject by causing an increase in peroxisome proliferator-activated receptor α (PPARα) activity by administering to a subject in need of such therapy, a therapeutic amount of the compound or composition described above. The compound may be provided in a composition formulated to provide a delayed release, controlled release, extended release, and/or sustained release of the compound. The disorder or condition may be retinal inflammation, retinal neovascularization, retinal vascular leakage, retinopathy of prematurity (ROP), diabetic retinopathy (DR), an age-related macular degeneration (AMD), or diabetic macular edema (DME). The disorder or condition may be characterized by inflammation and/or angiogenesis. The disorder or condition may be inflammatory bowel disease, type 1 diabetes, type 2 diabetes, Graves disease, multiple sclerosis, osteoarthritis, rheumatoid arthritis, vasculitis, dermatitis, glomerulonephritis, hepatitis, periodonititis, atherosclerosis, heart failure, obesity, Alzheimer's disease, or metabolic syndrome. The disorder or condition may be an ocular disorder or condition selected from keratitis, endophthalmitis, blepharitis, conjunctivitis, scleritis, herpetic inflammation, uveitis, vasculitis, arteritis, orbital inflammations, optic neuritis, sympathetic ophthalmia, retinitis, macular edema, glaucoma, proliferative vitreoretinopathy, corneal edema, uveal edema, and retinal edema. The disorder or condition may be a retinal artery or vein occlusion, corneal graft rejection, corneal neovascularization, neovascular glaucoma, sickle cell retinopathy, cancers, skin diseases, diabetic ulcers, diabetic nephropathy, cardiovascular disease, or stroke.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A compound, comprising chemical structure III:

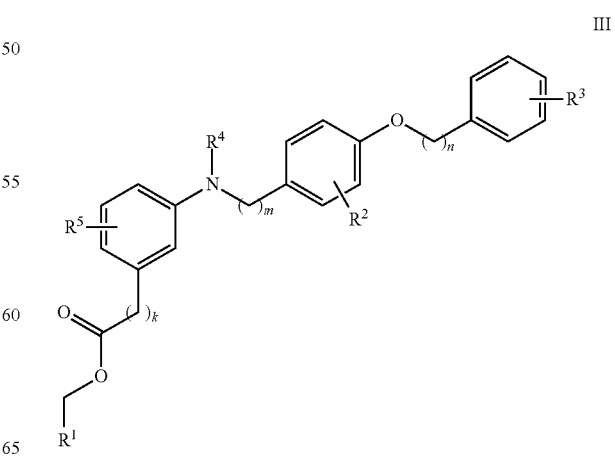

and salts and isomers thereof, wherein:
k is 0, 1, 2, 3, 4, 5, 6, 7, 8, 9, or 10 carbon atoms;
m is 0, 1, 2, 3, 4, or 5 carbon atoms;
n is 0, 1, 2, 3, 4, or 5 carbon atoms;
$R^1$ is selected from the group: phosphate and phosphonate;
$R^2$ is selected from the group: $CH_3$, hydrogen (H), chlorine (Cl), fluorine (F), bromine (Br), iodine (I), nitro ($NO_2$), $CH_2CH_3$, branched or unbranched alkyl chains with 3-10 carbon atoms, $OCH_3$, $OCH2CH3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^2$ comprises one, two, three, or four of said $R^2$ substituents substituted in any combination of said $R^2$ substituents and arranged in any pattern in the ring including ortho, meta, mono, di, tri, and tetrasubstituted;
$R^3$ is selected from the group: F, H, Cl, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^3$ comprises one, two, three, four, or five of said $R^3$ substituents substituted in any combination of said R3 substituents and arranged in any pattern in the ring including ortho, meta, para, mono, di, tri, tetra, and pentasubstituted;
$R^4$ is selected from the group: H, alkyl, and acyl; and
$R^5$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^5$ comprises one, two, three, or four of said $R^5$ substituents substituted in any combination of said $R_5$ substituents and arranged in any pattern in the ring including ortho, meta, para, mono, di, tri, and tetrasubstituted; and
wherein the compound has PPAα a agonistic activity.

2. The compound of claim 1, wherein $R^1$ is a phosphate having the chemical structure:

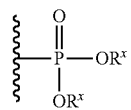

wherein each $R^X$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine.

3. The compound of claim 1, wherein $R^1$ is a phosphonate having the chemical structure:

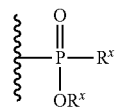

wherein each $R^X$ is independently selected from H, substituted alkyl, unsubstituted alkyl, substituted alkenyl, unsubstituted alkenyl, substituted alkynyl, unsubstituted alkynyl, substituted cycloalkyl, unsubstituted cycloalkyl, substituted heterocyclyl, unsubstituted heterocyclyl, substituted aryl, unsubstituted aryl, substituted heteroaryl, unsubstituted heteroaryl, substituted amine, and unsubstituted amine.

4. The compound of claim 1, having PPARα agonistic activity that is at least 1,000-fold greater than the compound's PPARγ agonistic activity or PPARδ agonistic activity.

5. A composition, comprising one or more compounds of claim 1 disposed in a pharmaceutically-acceptable carrier, vehicle, or diluent.

6. The composition of claim 5, formulated to provide a delayed release, controlled release, extended release, and/or sustained release of the one or more compounds.

7. A kit, comprising the composition of claim 5, and instructions for use thereof in a treatment of a disorder or condition in a subject.

8. The kit of claim 7, wherein the disorder or condition is an ocular disorder or condition selected from the group consisting of retinal inflammation, retinal neovascularization, retinal vascular leakage, retinopathy of prematurity (ROP), diabetic retinopathy (DR), an age-related macular degeneration (AMD), macular edema, diabetic macular edema (DME), keratitis, endophthalmitis, blepharitis, conjunctivitis, scleritis, herpetic inflammation, uveitis, vasculitis, arteritis, orbital inflammations, optic neuritis, sympathetic ophthalmia, retinitis, glaucoma, proliferative vitreoretinopathy, corneal edema, uveal edema, and retinal edema.

9. A method of increasing peroxisome proliferator-activated receptor α (PPARα) activity in a retinal cell, comprising: administering to the retinal cell a PPARα activity-enhancing amount of the compound of claim 1.

10. A method of treating a disorder or condition in a subject by causing an increase in peroxisome proliferator-activated receptor α (PPARα ) activity, comprising: administering to a subject in need of such therapy, a therapeutic amount of the compound of claim 1, wherein the compound is optionally provided in a composition formulated to provide a delayed release, controlled release, extended release, and/or sustained release of the compound.

11. The method of claim 10, wherein the disorder or condition is selected from the group consisting of retinal inflammation, retinal neovascularization, retinal vascular leakage, retinopathy of prematurity (ROP), diabetic retinopathy (DR), an age-related macular degeneration (AMD), and diabetic macular edema (DME).

12. The method of claim 10, wherein the disorder or condition is characterized by inflammation and/or angiogenesis.

13. The method of claim 10, wherein the disorder is selected from inflammatory bowel disease, type 1 diabetes, type 2 diabetes, Graves disease, multiple sclerosis, osteoarthritis, rheumatoid arthritis, vasculitis, dermatitis, glomerulonephritis, hepatitis, periodonititis, atherosclerosis, heart failure, obesity, Alzheimer's disease, and metabolic syndrome.

14. The method of claim 10, wherein the disorder or condition is an ocular disorder or condition selected from keratitis, endophthalmitis, blepharitis, conjunctivitis, scleritis, herpetic inflammation, uveitis, vasculitis, arteritis, orbital inflammations, optic neuritis, sympathetic ophthalmia, retinitis, macular edema, glaucoma, proliferative vitreoretinopathy, corneal edema, uveal edema, and retinal edema.

15. The method of claim 10, wherein the disorder or condition is selected from retinal artery or vein occlusion, corneal graft rejection, corneal neovascularization, neovascular glaucoma, sickle cell retinopathy, cancers, skin diseases, diabetic ulcers, diabetic nephropathy, cardiovascular disease, and stroke.

16. A compound, comprising chemical structure III:

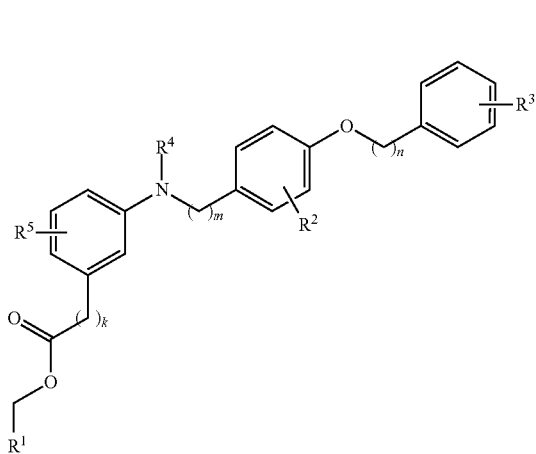

III and salts and isomers thereof, wherein:
k is 0, 1, or 2 carbon atoms;
m is 0, 1, or 2 carbon atoms;
n is 0, 1, or 2 carbon atoms;
$R_1$=phosphate or phosphonate;
$R_2$=H, 3-F, 3-Cl, 2-$CH_3$ or 3-$CH_3$;
$R_3$=4-F, 2,4-diF, 3,4-diF, 3,5-diF, or 4-$OCH_3$;
$R_4$=H or $CH_3$; and
$R_5$=H or F.

17. The compound of claim 16, wherein
k=1;
m=1;
n=1;
$R_1$=phosphate or phosphonate;
$R_2$=H, 3-F, 3-Cl, 2-$CH_3$ or 3-$CH_3$;
$R_3$=4-F, 2,4-diF, 3,4-diF, 3,5-diF, or 4-$OCH_3$;
$R_4$=H or $CH_3$; and
$R_5$=H or F.

18. The compound of claim 16, wherein
k=1;
m=1;
n=1;
$R_1$=phosphate or phosphonate;
$R_2$=H, 3-F, 3-Cl, 2-$CH_3$ or 3-$CH_3$;
$R_3$=4-F, 2,4-diF, 3,4-diF, 3,5-diF, or 4-$OCH_3$;
$R_4$=$CH_3$; and
$R_5$=H or F.

19. The compound of claim 16, wherein
k=1;
m=1;
n=1;
$R_1$=phosphate or phosphonate;
$R_2$=H, 3-F, 3-Cl, 2-CH3 or 3-$CH_3$;
$R_3$=4-F, 2,4-diF, 3,4-diF, 3,5-diF, or 4-$OCH_3$;
$R_4$=H; and
$R_5$=F.

20. The compound of claim 16, wherein
k=1;
m=1;
n=1;
R1 =phosphate or phosphonate;
$R_2$=2-$CH_3$ or 3-$CH_3$;
$R_3$=4-F, 2,4-diF, 3,4-diF, 3,5-diF, or 4-$OCH_3$;
$R_4$=H or $CH_3$; and
$R_5$=H or F.

21. The compound of claim 16, wherein
k=1;
m=1;
n=1;
$R_1$=phosphate or phosphonate;
$R_2$=H, 3-F, 3-Cl, 2-$CH_3$ or 3-$CH_3$;
$R_3$=4-F;
$R_4$=H or $CH_3$; and
$R_5$=H or F.

22. A method of increasing peroxisome proliferator-activated receptor α (PPARα) activity in a retinal cell, comprising: administering to the retinal cell a PPARα activity-enhancing amount of the compound of claim 16.

* * * * *